United States Patent
Brockmann et al.

(10) Patent No.: US 6,875,876 B2
(45) Date of Patent: *Apr. 5, 2005

(54) PROTECTED AMINOFUNCTIONALIZED POLYMERIZATION INITIATORS AND METHODS OF MAKING AND USING SAME

(75) Inventors: Thorsten Werner Brockmann, Gastonia, NC (US); Randy W. Hall, Kings Mountain, NC (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/322,926

(22) Filed: Dec. 18, 2002

(65) Prior Publication Data

US 2003/0162978 A1 Aug. 28, 2003

Related U.S. Application Data

(63) Continuation of application No. 09/665,528, filed on Sep. 19, 2000, now Pat. No. 6,610,859, which is a continuation-in-part of application No. 09/256,737, filed on Feb. 24, 1999, now Pat. No. 6,121,474.

(51) Int. Cl.$^7$ .................................................. C07F 1/02
(52) U.S. Cl. .................... 548/490; 564/373; 564/463
(58) Field of Search ................................. 564/373, 463; 564/353; 548/490

(56) References Cited

U.S. PATENT DOCUMENTS

| | | |
|---|---|---|
| 3,326,881 A | 6/1967 | Uraneck et al. |
| 3,776,964 A | 12/1973 | Morrison et al. |
| 3,842,146 A | 10/1974 | Milkovich et al. |
| 3,862,100 A | 1/1975 | Halasa et al. |
| 3,954,894 A | 5/1976 | Kamienski et al. |
| 4,039,593 A | 8/1977 | Kamienski et al. |
| 4,088,708 A | 5/1978 | Riew |
| 4,133,957 A | 1/1979 | Riew |
| 5,238,893 A | 8/1993 | Hergenrother et al. |
| 5,274,106 A | 12/1993 | Lawson et al. |
| 5,331,058 A | 7/1994 | Shepherd et al. |
| 5,391,663 A | 2/1995 | Bening et al. |
| 5,393,843 A | 2/1995 | Handlin, Jr. et al. |
| 5,405,911 A | 4/1995 | Handlin, Jr. et al. |
| 5,416,168 A | 5/1995 | Willis et al. |
| 5,491,230 A | 2/1996 | Lawson et al. |
| 5,496,940 A | 3/1996 | Lawson et al. |
| 5,523,364 A | 6/1996 | Engel et al. |
| 5,527,753 A | 6/1996 | Engel et al. |
| 5,550,203 A | 8/1996 | Engel et al. |
| 5,565,526 A | 10/1996 | Schwindeman et al. |
| 5,567,774 A | 10/1996 | Schwindeman et al. |
| 5,605,872 A | 2/1997 | Engel et al. |
| 5,798,418 A | 8/1998 | Quirk |
| 5,910,547 A | 6/1999 | Schwindeman et al. |
| 5,965,681 A | 10/1999 | Schwindeman et al. |

FOREIGN PATENT DOCUMENTS

| | | |
|---|---|---|
| DD | 242 232 A1 | 1/1987 |
| DD | 236 321 A1 | 6/1996 |
| EP | 0 725 069 A1 | 8/1996 |
| EP | 0 894 800 A2 | 2/1999 |
| GB | 2 255 567 | 11/1992 |
| WO | WO 97/05173 A | 2/1997 |
| WO | WO 97/05174 | 2/1997 |
| WO | WO 97/05176 | 2/1997 |
| WO | WO 97/05179 A | 2/1997 |
| WO | WO 97/05180 | 2/1997 |
| WO | WO 97/06188 A | 2/1997 |
| WO | WO 97/06192 | 2/1997 |
| WO | WO 97/16465 | 5/1997 |
| WO | WO 98/02465 | 1/1998 |
| WO | WO 00/50478 A0 | 8/2000 |

OTHER PUBLICATIONS

Faul et al., Liebigs Annalen der Chemie, 8, 1466–1473, 1986.*

Brown et al., "Indolisation of 1–decalone and the reactions of the products with oxygen and with nucleophiles," J. Chem. Soc., Perkin Trans. 1, no. 11, 1997, pp. 1699–1706.

* cited by examiner

Primary Examiner—Fiona T. Powers
(74) Attorney, Agent, or Firm—Myers Bigel Sibley & Sajovec, PA

(57) ABSTRACT

Anionic polymerization initiators useful in the preparation of polymers having a protected amine functional group. The amine functionality includes a first protecting group, which can be aralkyl, methyl, allyl or tertiary alkyl group. The other of the amine protecting groups can be the same as the first protecting group. Alternatively, the second protecting group can be different from the first protecting group, in which case it is selected to have differential stability to agents used to remove the aralkyl, methyl, allyl or tertiary alkyl protecting group.

14 Claims, No Drawings

PROTECTED AMINOFUNCTIONALIZED POLYMERIZATION INITIATORS AND METHODS OF MAKING AND USING SAME

CROSS REFERENCE TO RELATED APPLICATIONS

This application is a continuation of U.S. application Ser. No. 09/665,528, filed Sep. 19, 2000, which issued as U.S. Pat. No. 6,610,859, which is a continuation-in-part of U.S. application Ser. No. 09/256,737, filed Feb. 24, 1999, which issued as U.S. Pat. No. 6,121,474, the disclosures of which are incorporated by reference herein in their entireties.

FIELD OF THE INVENTION

The present invention relates to polymerization initiators, and more particularly to anionic polymerization initiators having protected amine functionality, as well as processes for making and using the same and polymers prepared using the initiators.

BACKGROUND OF THE INVENTION

Olefinic containing monomers can be polymerized using organo-alkali metal initiators, such as butyllithium. The resultant intermediate polymer contains an active alkali metal end group, which can be subsequently reacted with a suitable protonating, functionalizing, or coupling or linking agent to replace the alkali metal with a more stable end group. In many applications, it can be useful to react the polymer living end with a functionalizing agent, such as ethylene oxide, to provide a polymer having a terminal functional group, such as a hydroxyl, carboxyl, or amine group.

Telechelic polymers contain two functional groups per molecule at the termini of the polymer and are useful in a variety of applications. For example, telechelic polymers have been employed as rocket fuel binders, in coatings and sealants, and in adhesives. One approach that has been used to prepare telechelic polymers is the generation and subsequent functionalization of a "dilithium initiator." A dilithium initiator can be prepared by the addition of two equivalents of secondary butyllithium to meta-diisopropenylbenzene. The dilithium initiator is then reacted with suitable monomers, such as butadiene, to form a polymer chain with two anionic sites. The resultant polymer chain is then reacted with two equivalents of a functionalizing agent such as ethylene oxide.

While useful, gelation is frequently observed during the functionalization step. This leads to lower capping efficiencies (see, for example, U.S. Pat. No. 5,393,843, Example 1, wherein the capping efficiency was only 82%). Additional details of this gelation phenomena are described in U.S. Pat. No. 5,478,899. Further, this dilithium approach can only afford telechelic polymers with the same functional group on each end of the polymer chain.

Progress has been made in the synthesis of dihydroxy terminated polymers. For example, monofunctional silyl ether initiators containing alkali metal end groups are disclosed in GB 2,241,239. These monofunctional silyl ether initiators were demonstrated to be useful in producing polybutadienes having an alpha protected hydroxyl functional group. The living polymer can be reacted with suitable functionalizing agent such as ethylene oxide, and the silyl protecting group removed to provide a dihydroxy telechelic polymer.

Monofunctional ether initiators of the formula M—Z—O—C($R^1R^2R^3$) wherein M is an alkali metal, Z is a branched or straight chain hydrocarbon tether group, and $R^1$, $R^2$ and $R^3$ are independently defined as hydrogen, alkyl, substituted alkyl, aryl or substituted aryl, have also been proposed as anionic polymerization initiators to introduce a protected hydroxyl functionality into a polymer. See U.S. Pat. No. 5,621,149. The hydrocarbon solubility of such initiators can be increased by chain extension of the initiator with a conjugated diene. See U.S. Pat. No. 5,565,526.

Anionic initiators containing a tertiary amine functionality have also been proposed for use in hydrocarbon solvent polymerizations. Such initiators have the general formula

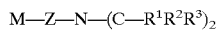

$$M-Z-N-(C-R^1R^2R^3)_2$$

wherein M is defined as an alkali metal selected from lithium, sodium and potassium; Z is defined as a branched or straight chain hydrocarbon connecting group which contains 3–25 carbon atoms; and $R^1$, $R^2$ and $R^3$ are independently defined as hydrogen, alkyl, substituted alkyl groups, aryl or substituted aryl groups. See M. J. Stewart, N. Shepherd, and D. M. Service, *Brit. Polym. J.*, 22, 319–325 (1990).

However, these amine functional initiators possess low solubility in hydrocarbon solvents (typically less than 0.3 Molar in aliphatic or cycloaliphatic solvents like hexane or cyclohexane). The addition of an ethereal co-solvent does increase the solubility of these initiators; however, this also increases the amount of 1,2-microstructure in the resultant polymer. See H. L. Hsieh and R. P. Quirk, *Anionic Polymerization Principles and Practical Applications*, pp. 397–400. Various other techniques have been employed to increase the solubility of these initiators in hydrocarbon solvent. For example, chain extension of the initiator with a conjugated diene increased the solubility several fold. See U.S. Pat. No. 5,527,753.

The synthesis of diamino terminated polymers remains relatively unexplored. Nakahama reports the preparation of amino terminated polystyrene by trapping the dianion with an electrophile that contained a protected amine group. A high degree of functionality was achieved by this technique. See K. Ueda, A. Hirao, and S. Nakahama, *Macromolecules*, 23, 939–945 (1990). However, the reaction conditions (−78° C., THF solvent) were not practical for commercial production of these functionalized polymers.

El-Aasser et al. recently reported the preparation of amino terminated telechelic polybutadiene by a free radical approach. See J. Xu, V. L. Dimonie, E. D. Sudol, and M. S. El-Aasser, *Journal of Polymer Science: Part A: Polymer Chemistry*, 33, 1353–1359 (1995). Since this is a free radical synthesis, little control of molecular weight, molecular weight distribution, and position of the amine functional group was obtained.

SUMMARY OF THE INVENTION

The present invention relates to protected amine functionalized initiators and processes for making and using the same to prepare amine functionalized polymers. The initiators of the invention include a tertiary amine functionality. The amine functionality includes two protecting groups, which may be the same or different. When the protecting groups are different, the groups are selected so as to have differential stability under specified deprotection conditions. Accordingly one of the protecting groups can be selectively removed without removing the other protecting group. In this manner, secondary amine functionalized polymers can be readily prepared.

Specifically the initiators of the invention include compounds of the formula:

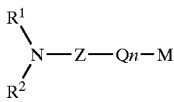

wherein:

M is an alkali metal selected from the group consisting of lithium, sodium and potassium;

Z is a branched or straight chain hydrocarbon connecting group which contains 3–25 carbon atoms, optionally substituted with aryl or substituted aryl;

Q is a saturated or unsaturated hydrocarbyl group derived by the incorporation of one or more unsaturated organic compounds, such as one or more compounds selected from the group consisting of conjugated diene hydrocarbons, alkenylsubstituted aromatic compounds, and mixtures thereof, into the M—Z linkage;

n is from 0 to 5;

$R^1$ is a protecting group selected from the group consisting of aralkyl, allyl, tertiary alkyl, and methyl; and $R^2$ can be the same as $R^1$, with the proviso that when $R^1$ is methyl, $R^2$ is not C1–C4 alkyl, or $R^2$ can be different from $R^1$, in which case $R^2$ is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, and substituted heterocycloalkyl, with the proviso that when $R^2$ is not the same as $R^1$, then $R^2$ is more stable under conditions used to remove $R^1$, or $R^1$ and $R^2$ together with the nitrogen atom to which they are attached form

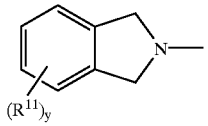

wherein y is from 1 to 4 and each $R^{11}$ is independently selected from the group consisting of hydrogen, alkyl, substituted alkyl, aryl, substituted aryl, cycloalkyl, substituted cycloalkyl, alkoxy, substituted alkoxy, heteroaryl, substituted heteroaryl, heterocycloalkyl, and substituted heterocycloalkyl.

In especially advantageous embodiments of the invention, the protecting group $R^1$ is aralkyl, preferably benzyl or a benzyl derivative; allyl; or tertiary alkyl, preferably tertiary butyl. In this aspect of the invention, advantageously $R^2$ is the same as $R^1$. Alternatively, in this aspect of the invention, $R^2$ is methyl. Examples of initiators of the invention include without limitation 3-[(N-benzyl-N-methyl)amino]1-propyllithium, 3-[(N,N-dibenzyl)amino]-1-propyllithium, 3-[(N-tert-butyl-N-methyl)amino]-1-propyllithium, 3-[(N,N-di-tert-butyl)amino]-1-propyllithium, and mixtures thereof.

These initiators can be treated with organometallic compounds, containing Mg, Zn, B, Al, and the like, to potentially afford higher solubility of the initiators in hydrocarbon solutions and/or living polymer stabilization. Other additives, such as those disclosed in copending U.S. Ser. No. 09/149,952, filed Sep. 9, 1998, and Ser. No. 09/512,494, filed Feb. 24, 2000, the entire disclosure of each of which is hereby incorporated by reference, can also be used to improve initiator solubility and/or living polymer stabilization.

The initiators are useful in polymerizing monomers capable of anionic polymerization, including but not limited to conjugated dienes such as butadiene and isoprene, alkenylsubstituted aromatic compounds such as styrene, and mixtures thereof, to generate mono-, homo- or heterotelechelic alpha amine functionalized polymers. The molecular weight of the polymers can vary widely, typically ranging from about 500 up to 10,000,000, although the polymers can have a molecular weight outside of this range as well. Advantageously the polymers have a molecular weight ranging from about 500 to about 20,000. The polymers can also have a variety of microstructures. For some applications, the polymers may have a 1,2 vinyl content ranging from about 20 to about 80%. Again, however, the invention includes polymers having a 1,2 vinyl content outside of this range, for example, from about 80% to about 100% 1,2 vinyl content or less than about 20% 1,2 vinyl content to the minimum 1,2 vinyl content that can be achieved (currently about 4–5%).

The polymers of the invention initially have an alpha tertiary amine functionality. The protecting group $R^1$ is selected so that the protecting group can be readily removed (or the amine functionality "deprotected") under select conditions suitable for removing the protecting group. For example, benzyl and benzyl derived protecting groups can be removed under conditions used to hydrogenate unsaturation in the polymer chain. An allyl protecting group can be removed utilizing a rhodium catalyst. Methyl protecting groups can be removed photochemically. Tertiary alkyl protecting groups can be removed by acid catalyzed deprotection techniques.

As noted above, $R^2$ can be the same as $R^1$. In this aspect of the invention, the resultant alpha tertiary amine functionalized polymers can be treated to substantially simultaneously remove both $R^1$ and $R^2$ to give a polymer having an alpha primary amine functionality.

Alternatively, $R^1$ and $R^2$ are not the same. In this aspect of the invention, $R^2$ is selected from suitable substituents which are more stable under the conditions used to remove $R^1$. As a result, $R^1$ can be removed while $R^2$ remains intact to give an alpha secondary amine functionalized polymer. The alpha secondary amine functionalized polymer can be further treated to remove $R^2$, thus giving an alpha primary amine functionalized polymer.

The living polymers can be further treated to quench or functionalize the living end thereof, for example, to provide near quantitative omega functionalized polymers (having for example hydroxyl, sulfide, carboxyl or other functionality). The polymers also have substantially homogeneous backbones, in contrast to polymers produced, for example, using dilithium initiator technology in which polymers include a cross linked core.

The polymers can be hydrogenated to give a liquid, processable functionalized polymer. In one advantageous aspect of the invention, an unsaturated polymer of the invention having a protected alpha tertiary amine functionality in which $R^1$ (and optionally $R^2$ as well) is benzyl or a benzyl derivative can be modified by replacing (or partially replacing) the protecting group with a hydrogen atom using hydrogenation to concurrently saturate the polymer and remove the benzyl protecting group(s) to afford a saturated polymer with an alpha primary or secondary amine functionality. The hydrogenation step can be performed for polymers having reactive or non-reactive functionality at the omega position of the polymer chain.

Thus the present invention provides polymers containing an alpha primary, secondary or tertiary amine functionality, optionally with a reactive or non-reactive functionality at the omega position of the polymer chain. Such polymers can be hydrogenated to afford a saturated (or partially saturated polymer) with an alpha primary, secondary or tertiary amine functionality. The protecting group can be present or displaced for the saturated or unsaturated polymers, depending upon the nature of the protecting group and the types of deprotection conditions required to remove the same.

Examples of the types of polymers, without limitation that can be prepared in accordance with the present invention are illustrated below:

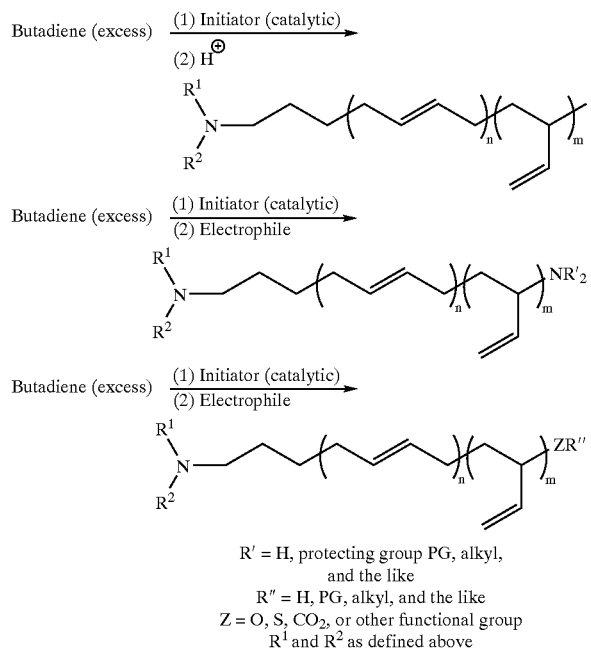

R' = H, protecting group PG, alkyl, and the like
R'' = H, PG, alkyl, and the like
Z = O, S, $CO_2$, or other functional group
$R^1$ and $R^2$ as defined above

DETAILED DESCRIPTION OF THE INVENTION

The present invention now will be described more fully hereinafter with reference to the preferred embodiments of the invention. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention provides novel anionic initiators, which can be hydrocarbon soluble, and mixtures of such initiators, containing a tertiary amino group and having the following general structure:

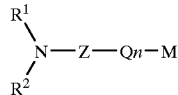

wherein:
M is an alkali metal selected from the group consisting of lithium, sodium and potassium;
Z is a branched or straight chain hydrocarbon connecting group which contains 3–25 carbon atoms, optionally substituted with aryl or substituted aryl;
Q is a saturated or unsaturated hydrocarbyl group, and can be derived by the incorporation of one or more unsaturated organic compounds, such as one or more compounds selected from the group consisting of conjugated diene hydrocarbons, alkenylsubstituted aromatic compounds, and mixtures thereof, into the M—Z linkage;
n is from 0 to 5;
$R^1$ is a protecting group selected from the group consisting of aralkyl, preferably benzyl or benzyl derivative, allyl, tertiary alkyl, preferably tertiary butyl, and methyl; and
$R^2$ can be the same as $R^1$, with the proviso that when $R^1$ is methyl, $R^2$ is not C1–C4 alkyl, or $R^2$ can be different from $R^1$, in which case $R^2$ is selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, and substituted heterocycloalkyl, with the proviso that when $R^2$ is not the same as $R^1$, then $R^2$ is more stable under conditions used to remove $R^1$,
or $R^1$ and $R^2$ together with the nitrogen atom to which they are attached form

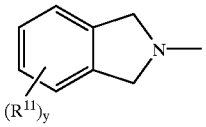

wherein y is from 1 to 4 and each $R^{11}$ is independently selected from the group consisting of hydrogen, alkyl, substituted alkyl, aryl, substituted aryl, cycloalkyl, substituted cycloalkyl, alkoxy, substituted alkoxy, heteroaryl, substituted heteroaryl, heterocycloalkyl, and substituted heterocycloalkyl.

The term "aralkyl" generally refers to aralkyl groups in which the total number of carbon atoms is no greater than about 18. The term aralkyl includes groups in which the alkylene chain and/or the aryl ring can include one or more heteroatoms, such as oxygen, nitrogen and sulfur. The alkylene chain and/or aryl ring can also be substituted with one or more groups such as C1–C4 alkyl, C1–C4 alkoxy, and the like, so long as the group does not interfere with the functionality of the benzyl protecting group and its removal, and/or with the activity of the lithium living end of the initiator.

Advantageous aralkyl groups in accordance with the invention are benzyl groups and benzyl derivatives. Benzyl derivatives include groups in which the phenyl ring is substituted with one or more groups such as C1–C4 alkyl, C1–C4 alkoxy, and the like, so long as the group does not interfere with the functionality of the benzyl protecting group and its removal, and/or with the activity of the lithium living end of the initiator. The term benzyl derivative also refers to benzyl groups in which the methylene linkage may also be substituted, for example, with one or more groups such as C1–C4 alkyl, C1–C4 alkoxy, aryl (phenyl) and the like, again so long as the group does not interfere with the functionality of the benzyl protecting group and its removal, and/or with the activity of the lithium living end of the initiator. Benzyl derivatives also include groups in which the ring and/or methylene chain can include heteroatoms, such as oxygen, sulfur or nitrogen. Such substituted benzyl protecting groups can be represented by the general formula:

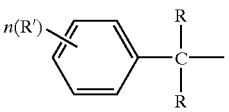

in which n is from 1 to 5; and each R and R' is independently selected from the group consisting of hydrogen, alkyl, substituted alkyl, aryl, substituted aryl, cycloalkyl, substituted cycloalkyl, alkoxy, substituted alkoxy, heteroaryl, substituted heteroaryl, heterocycloalkyl, substituted heterocycloalkyl, and the like, or at least one R in combination with the phenyl ring forms a cyclic or bicyclic structure, such as

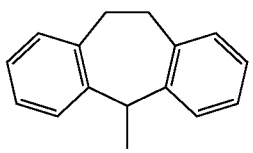

Exemplary R and R' groups include without limitation methoxy, phenyl, methoxyphenyl, and the like. Exemplary substituted benzyl substituents include without limitation 4-methoxybenzyl, 2,4-dimethoxybenzyl, diphenylmethyl, 4-methoxyphenylmethyl, triphenylmethyl, (4-methoxylphenyl)diphenylmethyl, and the like.

As used herein, the term "alkyl" refers to straight chain and branched C1–C25 alkyl. The term "substituted alkyl" refers to C1–C25 alkyl substituted with one or more lower C1–C10 alkyl, lower alkoxy, lower alkylthio, or lower dialkylamino. The term "cycloalkyl" refers to one or more rings, typically of 5, 6 or 7 atoms, which rings may be fused or unfused, and generally including 3 to 12 carbon atoms. The term "substituted cycloalkyl" refers to cycloalkyl as defined above and substituted with one or more lower C1–C10 alkyl, lower alkoxy, lower alkylthio, or lower dialkylamino. The term "aryl" refers to C5–C25 aryl having one or more aromatic rings, generally each of 5 or 6 carbon atoms. Multiple aryl rings may be fused, as in naphthyl or unfused, as in biphenyl. The term "substituted aryl" refers to C5–C25 aryl substituted with one or more lower C1–C10 alkyl, lower alkoxy, lower alkylthio, or lower dialkylamino. Exemplary aryl and substituted aryl groups include, for example, phenyl, benzyl, and the like. The term "alkoxy" refers to straight chain and branched C1–C25 alkoxy. The term "substituted alkoxy" refers to C1–C25 alkoxy substituted with one or more lower C1–C10 alkyl, lower alkoxy, lower alkylthio, or lower dialkylamino. The terms "heteroaryl" and "substituted heteroaryl" refer to aryl and substituted aryl as defined above which can include one to four heteroatoms, like oxygen, sulfur, or nitrogen or a combination thereof, which heteroaryl group is optionally substituted at carbon and/or nitrogen atom(s) with the groups such as noted above. The terms "heterocycloalkyl" and "substituted heterocycloalkyl" refer to cycloalkyl and substituted cycloalkyl as defined above having one or more rings of 5, 6 or 7 atoms with or without saturation or aromatic character and at least one ring atom which is not carbon. Exemplary heteroatoms include sulfur, oxygen, and nitrogen. Multiple rings may be fused or unfused.

The initiators of the invention are derived from omega-tertiary-amino-1-haloalkanes and mixtures thereof of the following general structures:

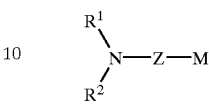

wherein X is halogen, preferably chlorine or bromine; and Z, $R^1$ and $R^2$ are as defined above. In the process, selected omega-tertiary-amino-1-haloalkanes, which alkyl groups contain 3 to 25 carbon atoms, are reacted with an alkali metal typically at a temperature between about 35° C. and about 130° C., preferably at the reflux temperature of an alkane, cycloalkane, or aromatic reaction solvent containing 5 to 12 carbon atoms and mixtures of such solvents. The resultant compound is a protected monofunctional organoalkali metal initiator that is not chain extended having the formula

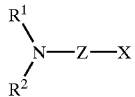

Tertiary amino-1-haloalkane raw materials (precursors) useful in the practice of this invention are commercially available or can be synthesized using commercially available compounds. For example, the precursor tertiary amino-1-haloalkanes can be prepared by the reaction of the corresponding amine with an alpha, omega dihalide, such as 1-bromo-3-chloro-propane or 1,6-dichloro-hexane. This synthetic method was originally described by J. Almena, F. Foubelo, and M. Yus, *Tetrahedron*, 51, 11883–11890 (1995). In this regard, substantially 1:1 molar ratios of the amine and dihaloalkane can be reacted in an inert or non-polar solvent, such as cyclohexane, optionally in the presence of a phase transfer catalyst, followed by addition of NaOH.

A variation of this chemistry was recently disclosed in co-pending application Ser. No. 08/882,513 (Docket 6055, filed Jun. 25, 1997), the entire disclosure of which is hereby incorporated by reference. See equation below:

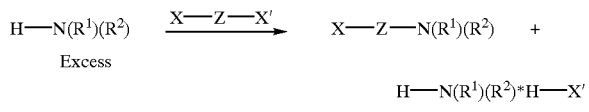

In this procedure, an excess of the amine starting material was reacted with an alpha, omega dihalide, such as 1-bromo-3-chloro-propane or 1,6-dichloro-hexane. The excess amine served as an acid scavenger for the acid liberated in the reaction. Each of these procedures afforded the desired precursor molecules in high yield, and in high purity. The precursors could be purified, if desired, by conventional techniques, such as chromatography, distillation, or recrystallization. Typically, the precursors could be employed directly in the subsequent metallation reaction.

Compounds in which $R^1$ and $R^2$ together with the nitrogen atom to which they are attached form

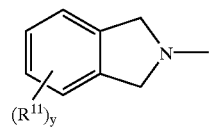

wherein y and $R^{11}$ are as defined above can also be prepared using a dihalo substrate

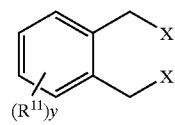

wherein each X is independently halo, and preferably each X is bromide. Such substrates are commercially available or can be prepared using known techniques. This dihalo substrate is reacted with the corresponding amine generally represented by the formula NH$_2$—Z—X, in which X is also halo and preferably Cl, and Z is as defined above (for example, —(CH$_2$)$_3$—), to prepare the halo amine precursor

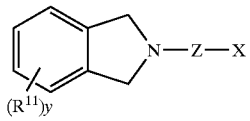

Amines NH$_2$—Z—X are also commercially available or can be synthesized using known techniques.

Examples of tertiary amino-1-haloalkanes raw materials (precursors) useful in the practice of this invention include, but are not limited to, 3-[(N-benzyl-N-methyl)amino]1-propylhalide, 3-[(N,N-dibenzyl)amino]-1-propylhalide, 3-[(N-tert-butyl-N-methyl)amino]-1-propylhalide, 3-[(N,N-di-tert-butyl)amino]-1-propylhalide, 3-[(N-allyl-N-methyl)amino]-1-propylhalide, 3-[(N,N-diallyl)amino]-1-propylhalide, 2-methyl-3-[(N-benzyl-N-methyl)amino]-1-propylhalide, 2-methyl-3-[(N,N-dibenzyl)amino]-1-propylhalide, 2-methyl-3-[(N-tert-butyl-N-methyl)amino]-1-propylhalide, 2-methyl-3-[(N,N-di-tert-butyl)amino]-1-propylhalide, 2-methyl-3-[(N-allyl-N-methyl)amino]-1-propylhalide, 2-methyl-3-[(N,N-diallyl)amino]-1-propylhalide, 2,2-dimethyl-3-[(N-benzyl-N-methyl)amino]-1-propylhalide, 2,2-dimethyl-3-[(N,N-dibenzyl)amino]-1-propylhalide, 2,2-dimethyl-3-[(N-tert-butyl-N-methyl)amino]-1-propylhalide, 2,2-dimethyl-3-[(N,N-di-tert-butyl)amino]-1-propylhalide, 2,2-dimethyl-3-[(N-allyl-N-methyl)amino]-1-propylhalide, 2,2-dimethyl-3-[(N,N-diallyl)amino]-1-propylhalide, 4-[(N-benzyl-N-methyl)amino]-1-butylhalide, 4-[(N,N-dibenzyl)amino]-1-butylhalide, 4-[(N-tert-butyl-N-methyl)amino]-1-butylhalide, 4-[(N,N-di-tert-butyl)amino]-1-butylhalide, 4-[(N-allyl-N-methyl)amino]-1-butylhalide, 4-[(N,N-diallyl)amino]-1-butylhalide, 6-[(N-benzyl-N-methyl)amino]-1-hexylhalide, 6-[(N,N-dibenzyl)amino]-1-hexylhalide, 6-[(N-tert-butyl-N-methyl)amino]-1-hexylhalide, 6-[(N,N-di-tert-butyl)amino]-1-hexylhalide, 6-[(N-allyl-N-methyl)amino]-1-hexylhalide, 6-[(N,N-diallyl)amino]-1-hexylhalide, 8-[(N-benzyl-N-methyl)amino]-1-octylhalide, 8-[(N,N-dibenzyl)amino]-1-octylhalide, 8-[(N-tert-butyl-N-methyl)amino]-1-octylhalide, 8-[(N,N-di-tert-butyl)amino]-1-octylhalide, 8-[(N-allyl-N-methyl)amino]-1-octylhalide, 8-[(N,N-diallyl)amino]-1-octylhalide, 3-[(N-methyl-N-C2–C25 alkyl or substituted alkyl)amino]-1-propylhalide, 2-methyl-3-[(N-methyl-N-C2–C25 alkyl or substituted alkyl)amino]-1-propylhalide, 2,2-dimethyl-3-[(N-methyl-N-C2–C25 alkyl or substituted alkyl)amino]-1-propylhalide, 4-[(N-methyl-N-C2–C25 alkyl or substituted alkyl)amino]-1-butylhalide, 6-[(N-methyl-N-C2–C25 alkyl or substituted alkyl)amino]-1-hexylhalide, 8-[(N-methyl-N-C2–C25 alkyl or substituted alkyl)amino]-1-octylhalide, 3-[(N-methyl-N-C5–C25 aryl or substituted aryl)amino]-1-propylhalide, 2-methyl-3-[(N-methyl-N-C5–C25 aryl or substituted aryl)amino]-1-propylhalide, 2,2-dimethyl-3-[(N-methyl-N-C5–C25 aryl or substituted aryl)amino]-1-propylhalide, 4-[(N-methyl-N-C5–C25 aryl or substituted aryl)amino]-1-butylhalide, 6-[(N-methyl-N-C5–C25 aryl or substituted aryl)amino]-1-hexylhalide, 8-[(N-methyl-N-C5–C25 aryl or substituted aryl)amino]-1-octylhalide, and the like and mixtures thereof. The halo- or halide group is selected from chlorine and bromine.

The alkali metal used in preparing the organometallic compounds containing tertiary amines, selected from lithium, sodium and potassium, is used as a dispersion whose particle size usually does not exceed about 300 microns. Preferably the particle size is between 10 and 300 microns although coarser particle size alkali metal can be used. When lithium metal is employed, the lithium metal can contain 0.2 to 5.0 and preferably 0.8 weight percent sodium. The alkali metal is used in amounts of 90% of theoretical to a 400% excess above the theoretical amount necessary to produce the compounds. The reaction temperature is greater than about 35° C. up to just below the decomposition of the reactants and/or the product. An abrasive can be optionally added to improve the metallation reaction. The yields of tertiary amino organometallic compounds prepared by this invention typically exceed 85%.

The organoalkali metal initiators of the formulae

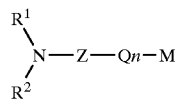

in which n is from greater than 0 to 5 are prepared by reacting a compound of the formulae

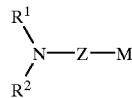

wherein M, Z, R$^1$, and R$^2$ have the meanings ascribed above, with one or more unsaturated organic compounds, such as one or more conjugated diene hydrocarbons, one or more alkenylsubstituted aromatic compounds, or mixtures of one or more dienes with one or more alkenylsubstituted aromatic compounds, to form an extended hydrocarbon chain between M and Z, which extended chain is denoted as Q$_n$. The non-chain extended initiator is reacted with a one or more conjugated diene hydrocarbons, one or more alkenyl-substituted aromatic compounds, or mixtures of one or more dienes with one or more alkenylsubstituted aromatic compounds, advantageously in a predominantly alkane, cycloalkane, or aromatic reaction solvent of 5 to 10 carbon atoms, and mixtures of such solvents, to produce a monofunctional initiator with an extended chain or tether between the metal atom M and Z and mixtures thereof with the non-chain extended compounds. The chain extension reaction can be performed in several different manifolds.

In one embodiment, a dilute solution of the non-chain extended initiator can be separated from solid excess alkali metal and co-product alkali metal halide (for example, the excess lithium metal and lithium chloride by-product when a lithium metal dispersion is used). The chain extension agent can then be added to the solution to increase the solubility of the non-chain extended initiator. Optionally, the concentration can be adjusted by removal of at least a portion of the solvent. In another embodiment, the chain extension agent is added to the reaction mixture prior to filtration to remove the excess alkali metal and co-product alkali metal halide.

The chain extension can be carried out under a variety of conditions. Generally the chain extension reaction can be conducted at temperatures ranging from about −30° C. to about 150° C. The chain extension may also be conducted in the presence of certain Lewis bases, generally at temperatures sufficient to slow down polymerization, relative to chain extension. In this aspect of the invention, the Lewis base may be one or more ethers, advantageously one or more aliphatic ethers, such as but not limited to diethyl ether, dimethyl ether, methyl tertiary butyl ether (MTBE), tetrahydrofuran (THF), 2-methyltetrahydrofuran, and the like and mixtures thereof. The Lewis base may also be one or more tertiary amines, such as aliphatic amines selected from the group consisting of trimethylamine, triethylamine, dimethylbutylamine, N,N,N',N'-tetramethylethylenediamine (TMEDA), and the like as well as mixtures thereof. The proportion of these Lewis bases to the organometallic being chain extended may be varied from about 0.05 mole to about 5.0 moles per mole of organometallic. The reaction temperature used in the presence of the Lewis base may be lowered to about −30° C. to about +30° C. to prevent attack by the organometallic on the Lewis base. As the skilled artisan will appreciate, however, the process conditions can depend on various factors such as the nature of Lewis base, the nature of the organometallic, and the ratio of the Lewis base to the organometallic, and can vary from the ranges given above.

In addition, as noted above, the chain extension reaction can be carried out either prior to isolation of the organometallic species from the solid excess alkali metal and co-product alkali metal halide, or subsequent to the filtration. It is noted that not all of the initiator must be chain extended, and the mixtures of chain extended and non-chain extended initiators can also provide benefits. It is also noted that less than one equivalent chain extension (i.e., n is greater than 0 but less than 1) can still provide hydrocarbon solubility and is contemplated to be within the scope of this invention.

The unsaturated organic chain extending compounds used in producing the initiators of this invention are chosen from the group of organic compounds that can be polymerized anionically in a reaction initiated by an alkali metal or its carbanionic derivative. Preferred are conjugated dienes and alkenyl substituted aromatic compounds, but other compounds can also be used in accordance with the present invention so long as the compound can form a chain extension.

Exemplary conjugated diene hydrocarbons include, but are not limited to, 1,3-butadiene, isoprene, 2,3-dimethyl-1,3-butadiene, 1,3-pentadiene (piperylene), myrcene, 2-methyl-3-ethyl-1,3-butadiene, 2-methyl-3-ethyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, 2,4-diethyl-1,3-butadiene, 2,3-di-n-propyl-1,3-butadiene, 2-methyl-3-isopropyl-1,3-butadiene, and the like and mixtures thereof. Other conjugated diene hydrocarbons can also be useful in practicing this invention, such as those disclosed in U.S. Pat. No. 3,377,404.

The polymerizable alkenylsubstituted aromatic hydrocarbons useful in producing the chain extended initiators of this invention include, but are not limited to, styrene, alpha-methylstyrene, vinyltoluene, 2-vinylpyridine, 4-vinylpyridine, 1-vinylnaphthalene, 2-vinylnaphthalene, 1-alpha-methylvinylnaphthalene, 2-alpha-methylvinylnaphathalene, 1,2-diphenyl-4-methyl-1-hexene, and the like and mixtures of these, as well as alkyl, cycloalkyl, aryl, alkaryl and aralkyl derivatives thereof in which the total number of carbon atoms in the combined hydrocarbon constituents is generally not greater than 18. Examples of these latter compounds include without limitation 3-methylstyrene, 3,5-diethylstyrene, 2-ethyl-4-benzylstyrene, 4-phenylstyrene, 4-p-tolylstyrene, 2,4-divinyltoluene, 4,5-dimethyl-1-vinylnaphthalene, and the like and mixtures thereof. Reference is made to U.S. Pat. No. 3,377,404 for disclosure of additional alkenyl substituted aromatic compounds. Non-polymerizable conjugated dienes and alkenyl substituted aromatic compounds including but not limited to 1,1-diphenylethylene and 2,4-hexadiene may also be employed as chain extension agents in accordance with the present invention.

The inert solvent employed during the preparation of the initiators of the present invention, or in subsequent polymerizations as discussed in more detail below, for some applications is preferably a non-polar solvent such as a hydrocarbon, since anionic polymerization in the presence of such non-polar solvents is known to produce polyenes with high 1,4-contents from 1,3-dienes. Inert hydrocarbon solvents useful in practicing this invention include but are not limited to inert liquid alkanes, cycloalkanes, aromatic solvents and mixtures thereof. Exemplary alkanes and cycloalkanes can contain five to ten carbon atoms, such as but not limited to pentane, hexane, cyclohexane, methylcyclohexane, heptane, methylcycloheptane, octane, decane and the like as well as mixtures thereof. Exemplary aromatic solvents can contain six to ten carbon atoms, such as but not limited to benzene, toluene, ethylbenzene, p-xylene, m-xylene, o-xylene, n-propylbenzene, isopropylbenzene, n-butylbenzene, and the like, and mixtures thereof.

While the compounds have been described herein as useful as anionic polymerization initiators, it is noted that the compounds of the invention as not so limited in use and can also be useful as reagents in a variety of synthesis applications.

The present invention also provides a process for the anionic polymerization of anionically polymerizable monomers. The process of the invention includes the step of initiating polymerization of one or more monomers or compounds that can be anionically polymerized. Exemplary anionically polymerizable compounds include conjugated diene hydrocarbon monomers, a mixture of conjugated diene monomers, alkenyl substituted aromatic compounds, a mixture of alkenyl substituted aromatic compounds, or a mixture of one or more conjugated diene hydrocarbons and one or more alkenyl substituted aromatic compounds.

Other anionically polymerizable compounds can also be used as known in the art, singly or in combination with one another or with other types of monomer(s). For example, the monomers can include one or more polar monomers such as, without limitation, esters, amides, and nitriles of acrylic and methacrylic acid, and mixtures thereof with one another and/or with other monomers. Examples of polar monomers include without limitation methyl methacrylate, methyl acrylate, t-butyl methacrylate, t-butyl acrylate, ethyl methacrylate, N,N-dimethylacrylamide, lauryl methacrylate, stearyl methacrylate, 2,3-epoxypropyl methacrylate, decyl methacrylate, and octyl methacrylate. For reference, see Macromolecules, 14, 1599 (1981); Polymer 31, 106 (1990); Polymer, 34, 2875 (1993). See also U.S. Pat. No. 5,900,464.

The polymers of the invention can also include silicone block(s). Such blocks can be prepared by anionically polymerizing one or more cyclic siloxane monomers as known in the art. See U.S. Pat. No. 6,020,430. Generally such monomers can be defined by the formula $(R^1R^2SiO)_y$, wherein $R^1$ and $R^2$ are each independently selected from the group consisting of hydrogen, alkyl, substituted alkyl, alkenyl, substituted alkenyl, aryl, and substituted aryl and $y=3-10$.

Additional anionically polymerizable monomers include olefins such as ethylene, porpylene, and the like. See U.S. Pat. No. 5,849,847.

The monomer(s) are polymerized in a hydrocarbon or mixed hydrocarbon-polar solvent medium generally at a temperature of 10° C. to 150° C. with one or more initiators having the formula:

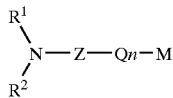

wherein $R^1$, $R^2$, Z, Q, n and M are as defined above. This provides an intermediate living polymer of the formula:

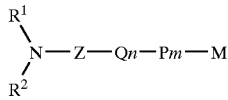

wherein:
P is a saturated or unsaturated hydrocarbyl group derived by incorporation of one or more anionically polymerizable compounds, such as but not limited to, one or more compounds selected from the group consisting of conjugated diene hydrocarbons, alkenylsubstituted aromatic compounds, and mixtures thereof;
m is from 2 to 20,000; and
M, Q, Z, $R^1$, $R^2$, and n have the meanings ascribed above.
The intermediate living polymer is then reacted with a suitable protonating, functionalizing, or coupling or linking agent, as known in the art.

In one aspect of the invention, the living polymer is reacted with a functionalizing agent (or electrophile) of the formula $$X—Y—T—(A—R^4R^5R^6)_k$$

wherein:
X is halide selected from the group consisting of chloride, bromide and iodide;
Y is a branched or straight chain hydrocarbon connecting group which contains 1–25 carbon atoms, optionally substituted with aryl or substituted aryl;
T is selected from the group consisting of oxygen, sulfur, and nitrogen and mixtures thereof;
A is an element selected from Group IVa of the Periodic Table of the Elements;
$R^4$, $R^5$, and $R^6$ are each independently selected from the group consisting of hydrogen, alkyl, substituted alkyl, aryl, substituted aryl, cycloalkyl, and substituted cycloalkyl, or $R^6$ is optionally a —$(CR^7R^8)_l$— group linking two A when k is 2, wherein $R^7$ and $R^8$ are each independently selected from the group consisting of hydrogen, alkyl, substituted alkyl, aryl, substituted aryl, cycloalkyl, and substituted cycloalkyl, and l is an integer from 1 to 7; and
k is 1 when T is oxygen or sulfur, and 2 when T is nitrogen. Thus the skilled artisan will appreciate that $R^6$ as used herein includes the group

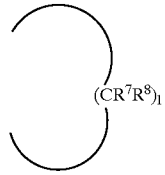

linking two A groups when k is 2.

The functionalizing agents can be prepared as described, for example, in International Publication WO 97/16465, the entire disclosure of which is incorporated by reference. In addition, the electrophiles can be prepared as described in K. Ueda, A. Hirao, and S. Nakahama, Macromolecules, 23, 939 (1990); U.S. Pat. Nos. 5,496,940; 5,600,021; 5,362,699; A. Alexakis, M. Gardette, and S. Colin, Tetrahedron Letters, 29, 1988, 2951; B. Figadere, X. Franck, and A. Cave, Tetrahedron Letters, 34, 1993, 5893; J. Almena, F. Foubelo, and M. Yus, Tetrahedron, 51, 1995, 11883; D. F. Taber and Y. Wang, J. Org. Chem., 58, 1993, 6470; F. D. Toste and I. W. J. Still, Synlett, 1995, 159; and U.S. Pat. No. 5,493,044. The functionalization step can be conducted at temperatures ranging from about −30° C. to about 150° C.

Other compounds useful in functionalizing living polymers include, but are not limited to, alkylene oxides, such as ethylene oxide, propylene oxide, styrene oxide, and oxetane; oxygen; sulfur; carbon dioxide; halogens such as chlorine, bromine and iodine; propargyl halides; alkenylhalosilanes and omega-alkenylarylhalosilanes, such as styrenyldimethyl chlorosilane; sulfonated compounds, such as 1,3-propane sultone; amides, including cyclic amides, such as caprolactam, N-benzylidene trimethylsilylamide, and dimethyl formamide; silicon acetals; 1,5-diazabicyclo[3.1.0] hexane; allyl halides, such as allyl bromide and allyl chloride; methacryloyl chloride; amines, including primary, secondary, tertiary and cyclic amines, such as 3-(dimethylamino)-propyl chloride and N-(benzylidene) trimethylsilylamine; haloalkyltrialkoxysilanes; epihalohydrins, such as epichlorohydrin, epibromohydrin, and epiiodohydrin, and other materials as known in the art to be useful for terminating or end capping polymers. These and other useful functionalizing agents are described, for example, in U.S. Pat. Nos. 3,786,116 and 4,409,357, the entire disclosure of each of which is incorporated herein by reference.

Other particularly advantageous functionalizing agents are imines. Imines are generally known in the art and can be described as having the general formula:

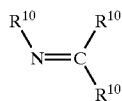

wherein each $R^{10}$ is independently selected from the group consisting of hydrogen, alkyl, substituted alkyl, aryl, substituted aryl, cycloalkyl, substituted cycloalkyl, alkoxy, substituted alkoxy, heteroaryl, substituted heteroaryl, heterocycloalkyl, substituted heterocycloalkyl, and alkylsilyl (such as trimethylsilyl). Exemplary imine functionalizing agents include without limitation N-(benzylidene) trimethylsilylamine

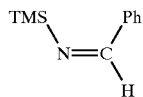

(in which TMS is trimethylsilyl and Ph is phenyl); and N-(benzylidene)methylamine

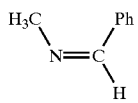

Examples of difunctional coupling agents useful to form protected telechelic polymers include, but are not limited to, Me$_2$SiCl$_2$, Me$_2$Si(OMe)$_2$, Me$_2$SnCl$_2$, Ph$_2$SiCl$_2$, MePhSiCl$_2$, ClMe$_2$SiCH$_2$CH$_2$SiMe$_2$Cl, and Me$_2$SiBr$_2$, and the like and mixtures thereof.

Examples of useful multifunctional linking or coupling agents include isomeric (mixtures of ortho, meta and para) dialkenylaryls and isomeric di- and trivinylaryls, such as 1,2-divinylbenzene, 1,3-divinylbenzene, 1,4-divinylbenzene, 1,2,4-trivinylbenzenes, 1,3-divinylnaphthalenes, 1,8-divinylnaphthalene, 1,2-diisopropenylbenzene, 1,3-diisopropenylbenzene, 1,4-diisopropenylbenzene, 1,3,5-trivinylnaphthalene, and other suitable materials known in the art to be useful for coupling polymers, as well as mixtures of coupling agents. Other exemplary multifunctional linking or coupling agents include halosilanes, halostannanes, phosphorus halides, and the like and mixtures thereof. Examples of the same include without limitation tin tetrachloride (SnCl$_4$), silicon tetrachloride (SiCl$_4$), methyl trichlorosilane (MeSiCl$_3$), HSi(OMe)$_3$, Si(OEt)$_4$, Cl$_3$SiSiCl$_3$, phosphorus trichloride and the like and mixtures thereof. See also U.S. Pat. Nos. 3,639,517 and 5,489,649, and R. P. Zelinski et al in J. Polym.Sci., A3, 93, (1965) for these and additional coupling agents. Mixtures of coupling agents can also be used. Generally, the amount of coupling agent used is such that the molar ratio of protected living polymer anions to coupling agents ranges from 1:1 to 24:1. This linking process is described, for example, in U.S. Pat. No. 4,409,357 and by L. J. Fetters in Macromolecules, 9,732 (1976).

The resultant polymer thus can be a linear, homotelechelic, heterotelechelic, branched, or radial polymer having one or more terminal tertiary amino functional groups. The polymer can be recovered from the reaction media and optionally hydrogenated and/or deprotected.

If a mixture of monomers is employed in the polymerization, the monomers can be added together to afford random or tapered block copolymers. The monomers can also be charged to the reactor sequentially to afford block copolymers.

Monomer(s) to be anionically polymerized to form living polymer anions can be selected from any suitable monomer capable of anionic polymerization, including conjugated alkadienes, alkenylsubstituted aromatic hydrocarbons, and mixtures thereof. Examples of suitable conjugated alkadienes include, but are not limited to, 1,3-butadiene, isoprene, 2,3-dimethyl-1,3-butadiene, 1,3-pentadiene, myrcene, 2-methyl-3-ethyl-1,3-butadiene, 2-methyl-3-ethyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, 2,4-diethyl-1,3-butadiene, 2,3-di-n-propyl-1,3-butadiene, and 2-methyl-3-isopropyl-1,3-butadiene.

Examples of polymerizable alkenylsubstituted aromatic hydrocarbons include, but are not limited to, styrene, alpha-methylstyrene, vinyltoluene, 2-vinylpyridine, 4-vinylpyridine, 1-vinylnaphthalene, 2-vinylnaphthalene, 1-alpha-methylvinylnaphthalene, 2-alpha-methylvinylnaphthalene, 1,2-diphenyl-4-methyl-1-hexene and mixtures of these, as well as alkyl, cycloalkyl, aryl, alkylaryl and arylalkyl derivatives thereof in which the total number of carbon atoms in the combined hydrocarbon constituents is generally not greater than 18. Examples of these latter compounds include 3-methylstyrene, 3,5-diethylstyrene, 4-tert-butylstyrene, 2-ethyl-4-benzylstyrene, 4-phenylstyrene, 4-p-tolylstyrene, 2,4-divinyltoluene and 4,5-dimethyl-1-vinylnaphthalene. U.S. Pat. No. 3,377,404, incorporated herein by reference in its entirety, discloses suitable additional alkenylsubstituted aromatic compounds.

The inert solvent is preferably a non-polar solvent such as a hydrocarbon, since anionic polymerization in the presence of such non-polar solvents is known to produce polyenes with high 1,4-contents from 1,3-dienes. Inert hydrocarbon solvents useful in practicing this invention include but are not limited to inert liquid alkanes, cycloalkanes and aromatic solvents and mixtures thereof. Exemplary alkanes and cycloalkanes include those containing five to 10 carbon atoms, such as pentane, hexane, cyclohexane, methylcyclohexane, heptane, methylcycloheptane, octane, decane and the like and mixtures thereof. Exemplary aryl solvents include those containing six to ten carbon atoms, such as toluene, ethylbenzene, p-xylene, m-xylene, o-xylene, n-propylbenzene, isopropylbenzene, n-butylbenzene, and the like and mixtures thereof.

Polar solvents (modifiers), however, can be added to the polymerization reaction to alter the microstructure of the resulting polymer, i.e., increase the proportion of 1,2 (vinyl) microstructure or to promote functionalization or randomization. For certain applications, it can be advantageous to provide polymers having from 20 to 80% 1,2 vinyl microstructure. Examples of polar modifiers include, but are not limited to: diethyl ether, dibutyl ether, tetrahydrofuran (THF), 2-methyltetrahydrofuran, methyl tert-butyl ether (MTBE), diazabicyclo[2.2.2]octane (DABCO), triethylamine, tri-n-butylamine, N,N,N',N'-tetramethylethylenediamine (TMEDA), and 1,2-dimethoxyethane (glyme). The amount of the polar modifier added depends on the vinyl content desired, the nature of the monomer, the temperature of the polymerization, and the identity of the polar modifier. The polar solvent (modifier) can be added to the reaction medium at the beginning of the polymerization as part of the solvent reaction medium, added during the polymerization or after polymerization but prior to functionalization or coupling.

Unsaturation in the polymer chain may be treated as known in the art to modify the same. For example, the unsaturated polymer may be reacted with one or more epoxides to form one or more epoxy groups along the backbone thereof.

The polymers produced may be optionally hydrogenated to afford additional novel, functionalized polymers. Examples of methods to hydrogenate the polymers of this invention are described in Falk, *Journal of Polymer Science: Part A-1*, vol. 9, 2617–2623 (1971), Falk, *Die Angewandte Chemie*, 21, 17–23 (1972), U.S. Pat. Nos. 4,970,254, 5,166,277, 5,393,843, 5,496,898, and 5,717,035. The hydrogenation of the functionalized polymer is conducted in situ, or in a suitable solvent, such as hexane, cyclohexane or heptane. This solution is contacted with hydrogen gas in the presence of a catalyst, such as a nickel catalyst. The hydrogenation is typically performed at temperatures from 25° C. to 150° C., with an archetypal hydrogen pressure of 15 psig to 1000 psig. The progress of this hydrogenation can be monitored by InfraRed (IR) spectroscopy or Nuclear Magnetic Resonance (NMR) spectroscopy. The hydrogenation reaction can be conducted until at least 90% of the aliphatic unsaturation has been saturated. The hydrogenated functional polymer is then recovered by conventional procedures, such as removal of the catalyst with aqueous acid wash, followed by solvent removal or precipitation of the polymer.

The protecting group can be removed from the functionalized polymer, if desired. This deprotection can be conducted either prior to or subsequent to the optional hydrogenation of the aliphatic unsaturation. Deprotection of these polymers affords a linear or radial polymer which contain either a mono-, di- or multifunctional terminal primary or secondary amino group.

When the protecting group $R^1$ (and optionally $R^2$) is aralkyl, and preferably benzyl or benzyl derivative, then deprotection and hydrogenation can be performed concurrently. In this aspect of the invention, the polymer can be partially hydrogenated under conditions selected to leave the benzyl or benzyl derived protecting group intact. Alternatively the polymer can be partially hydrogenated so as to remove the benzyl or benzyl derived protecting group, yet substantially hydrogenate unsaturation in the polymer chain.

Various methods can be employed for the removal of the other tertiary alkyl, such as tertiary butyl, allyl, or methyl protecting groups. For example, to remove tert-alkyl-protecting groups, the protected polymer is mixed with Amberlyst® 15 ion exchange resin and heated at an elevated temperature, for example 150° C., until deprotection is complete. In addition, tert-alkyl-protecting groups can also be removed by reaction of the polymer with trifluoroacetic acid, or trimethylsilyliodide. Additional methods of deprotection of the tert-alkyl protecting groups can be found in T. W. Greene and P. G. M. Wuts, Protective Groups in Organic Synthesis, 3d Edition, Wiley, New York, 1999, page 574. See also U.S. Pat. No. 5,922,810, issued Jul. 13, 1999.

As noted above, aralkyl, such as benzyl and benzyl derived protecting groups, can be removed under conditions used to hydrogenate polymers. See T. W. Greene and P. G. M. Wuts, Protective Groups in Organic Synthesis, 3d Edition, Wiley, New York, 1999, pages 577–585 for this and other deprotection techniques for aralkyl protecting groups. Hydrogenation may also be used to remove the protecting group

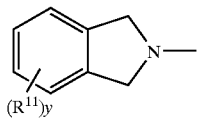

as defined above to liberate the nitrogen atom. It is noted that hydrogenation conditions can be selected so as to partially hydrogenate the polymer and leave the aralkyl, for example benzyl or benzyl derivative, intact.

The allyl protecting group can be removed utilizing a rhodium catalyst. See B. C. Laguzza and B. Ganem, Tetrahedron Lett., 22, 1483 (1981). Reference is also made to T. W. Greene and P. G. M. Wuts, Protective Groups in Organic Synthesis, 3d Edition, Wiley, New York, 1999, pages 574–76.

Methyl protecting groups can be removed photochemically. For example, the methyl protecting groups can be cleaved or removed photochemically in the presence of an electron acceptor such as 9,10-dicyanoanthracene. J. Santamaria, R. Ouchabane, and J. Rigaudy, Tetrahedron Lett., 30, 2927 (1989). Reference is also made to T. W. Greene and P. G. M. Wuts, Protective Groups in Organic Synthesis, 3d Edition, Wiley, New York, 1999, pages 573–74.

After deprotection, the degree of functionality of the amino polymer can be determined by the method of J. S. Fritz and G. H. Schenk, Quantitative Analytical Chemistry, 3rd edition; Allyn and Bacon, Inc.: Boston, 1974, p. 1974. The polymer was dissolved in a 1/1 mixture of chloroform and glacial acetic acid, and titrated with perchloric acid, and with methyl violet as the indicator. The deprotection is generally near quantitative to provide an amine functionality of about I, or when a protected amine functionalized electrophile is used, about 2 for linear polymers.

The resultant polymer can be a linear monofunctional polymer (resulting from quench of the living polymer with a protonating agent). The polymer can also be a linear telechelic polymer having two protected functional groups, in which the protecting group(s) and/or protected functionalities can be the same or different. Polymers possessing similarly protected functional groups can be deprotected by selecting a reagent specifically suited to remove the similar protecting groups. Alternatively, the invention also provides a process for the preparation of a linear polymer possessing one free telechelically functional group and one protected telechelically functional group. In this aspect of the invention, one type of protecting group is selectively deprotected from a dissimilarly protected functionality on the end(s) of the arms of the linear polymer chains, produced as described above, using selective reagents specifically suited to remove the targeted protective group and liberate the desired functionality, on the end of the polymer chain.

In yet another aspect of the invention, star or multi-branched polymers are produced by linking the living polymer anions using a coupling or linking agent as known in the art (for example the multifunctional linking agents as described above). The star polymers can be prepared using the protected amine initiators of the present invention and mixtures of these initiators with one another as well as with other protected functionalized initiators having different protecting groups and/or different protected functionalities. See, for example, U.S. Pat. Nos. 5,527,753, 5,827,929; 5,821,307; 5,919,870; 5,798,418; and 5,780,551, for a discussion of various protected functionalized initiators and star or multi-branched polymers made using various initiators. In addition, other types of protected functionalized initiators and/or non-functional initiators as known in the art can also be used in combination with the initiators of the present invention. The resultant polymers can have 3 to 30 arms. The protecting groups of the arms of the resultant star polymers can be removed, as discussed above, including the selective deprotection of dissimilar protecting groups.

The following table details experimental conditions that will selectively remove one of the protecting groups (more labile) from the polymer, while retaining the other protecting group (more stable).

| LABILE | STABLE | CONDITIONS |
| --- | --- | --- |
| t-Butyldimethylsilyl | t-Butyl | Tetrabutylammonium fluoride |
| t-Butyldimethylsilyl | t-Butyl | 1 N HCl |
| t-Butyldimethylsilyl | Dialkylamino | Tetrabutylammonium fluoride |
| t-Butyldimethylsilyl | Dialkylamino | 1 N HCl |
| t-Butyl | Dialkylamino | Amberlyst ® resin |
| t-Amyl | Dialkylamino | Amberlyst ® resin |
| Trimethylsilyl | t-Butyl | Tetrabutylammonium fluoride |
| Trimethylsilyl | t-Butyl | 1 N HCl |
| Trimethylsilyl | Dialkylamino | Tetrabutylammonium fluoride |
| Trimethylsilyl | Dialkylamino | 1 N HCl |
| 2,2,5,5-Tetramethyl-2,5-disila-1-azacyclopentane | t-Butyl | Tetrabutylammonium Fluoride |
| 2,2,5,5-Tetramethyl-2,5-disila-1-azacyclopentane | t-Butyl | 1 N HCl |

-continued

| LABILE | STABLE | CONDITIONS |
|---|---|---|
| 2,2,5,5-Tetramethyl-2,5-disila-1-azacyclopentane | Dialkylamino | Tetrabutylammonium Fluoride |
| 2,2,5,5-Tetramethyl-2,5-disila-1-azacyclopentane | Dialkylamino | 1 N HCl |

In another aspect of this invention, unique polymers produced by the process described above are provided. The polymers produced by this process may have linear, branched or radial architecture. Further, the polymers may be monofunctional (produced by quench of the living anion), homotelechelic (for example, produced by coupling of the living anion with a coupling agent with two active sites or by trapping of the living polymer anion with a protected, functionalized electrophile electrophile), heterotelechelic (produced by quench of the living polymer anion with an electrophile), or polyfunctional (produced by coupling of the living anion with a coupling agent with more than two active sites, such as tin tetrachloride or diisopropenylbenzene).

For example, exemplary monofunctional and telechelic polymers of the invention are represented by the formulas below:

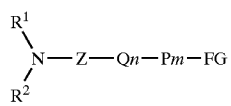

wherein:

Q, Z, $R^1$, $R^2$, and n have the meanings ascribed above;

P is a saturated or unsaturated hydrocarbyl group derived by incorporation of one or more anionically polymerizable compounds, such as but not limited to compounds selected from the group consisting of conjugated dienes, alkenylsubstituted aromatic hydrocarbons and mixtures thereof;

m is from 2 to 20,000; and

FG is hydrogen or a protected or unprotected functional group. Alternatively, FG can be a polymer segment derived by reaction of a functional group with at least one comonomer.

The skilled artisan will appreciate that monofunctional polymers result when FG is hydrogen, produced by quench of the living anion. The resultant mono-functionalized polymer can be treated to remove one of the protecting groups (when $R^1$ and $R^2$ are not the same) or to remove both protecting groups in one step (for example when $R^1$ and $R^2$ are the same) or sequentially (when $R^1$ and $R^2$ are not the same and are removed under different conditions). Removing one protecting group provides an alpha secondary amine functionalized polymer of the formula

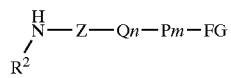

while removing both protecting groups (either simultaneously or sequentially) provides an alpha primary amine functionalized polymer of the formula

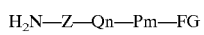

The skilled artisan will appreciate that FG can also be a protected or non-protected functional group or a polymer segment derived by incorporation of one or more comonomers with a functional group.

Telechelic polymers (both homotelechelic and heterotelechelic) can be prepared by reaction of the living polymer with any of the types of functionalizing agents or electrophiles as known in the art described in more detail above. For example, homotelechelic polymers can be produced by trapping of the living polymer anion with a protected, functionalized electrophile. Heterotelechelic polymers include those polymers in which FG and the omega protected amine functionality are different. In one aspect of the invention, heterotelechelic polymers include polymers which have been terminated using a functionalizing agent (or electrophile) of the formula X—Y—T—(A—$R^4R^5R^6$)k wherein X, Y, T, A, $R^4$, $R^5$, $R^6$ and k are the same as defined above. Exemplary polymers functionalized with such an electrophile can have the structure below:

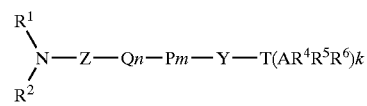

wherein Y, Z, T, A, P, Q, k, m, n, $R^1$, $R^2$, $R^4$, $R^5$, and $R^6$ are the same ascribed above (i.e., FG is —Y—T—(A($R^4R^5R^6$)k). In one advantageous embodiment of the invention the polymer has the formula:

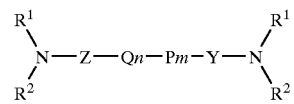

wherein Y, Z, P, Q, m, n, $R^1$, and $R^2$ are the same ascribed above.

The protected linear functionalized polymers can be treated to remove one, two or more protecting groups as described above. The resultant deprotected functionalized polymers can have the following structures:

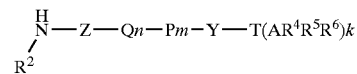

(removal of $R^1$ alone),

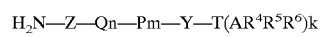

(simultaneous or sequential removal of $R^1$ and $R^2$),

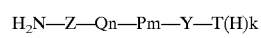

(simultaneous or sequential removal of $R^1$, $R^2$ and —$AR^4R^5R^6$),

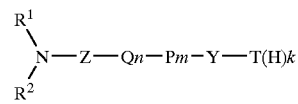

(removal of —$AR^4R^5R^6$), and

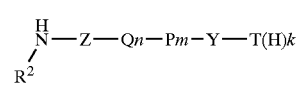

(removal of $R^1$ and —$AR^4R^5R^6$).

In a particularly advantageous embodiment of the invention, the polymer includes two $R^1$ protecting groups which are the same and both $R^1$s are removed to provide an alpha, omega secondary diamine functionalized polymer of the formula $$NH-Z-Qn-Pm-Y-NH$$
with $R^2$ on each NH In another aspect of the invention, heterotelechelic polymers include polymers which have been terminated using an imine functionalizing agent (or electrophile) of the formula $$R^{10}_2C=N-R^{10}$$

wherein each $R^{10}$ is as defined above. The resultant polymer functionalized with an imine electrophile can have the structure below:

$$R^1R^2N-Z-Qn-Pm-C(R^{10})_2-N(R^{10})H$$

wherein $R^1$, $R^2$, Z, Q, n, P, m, and $R^{10}$ have the meanings as set forth above. One, two or more protecting groups can be removed in this aspect of the invention as well.

One exemplary polymer of this aspect of the invention has the formula $$R^1R^2N-Z-Qn-Pm-CH(Ph)-N(Me)H$$

wherein Ph is phenyl and Me is methyl. In this aspect of the invention, when $R^1$ is methyl, the polymer can be treated remove both methyl groups to provide a diamine functionalized polymer having a secondary amine functionality and a primary amine functionality, i.e., $$HN(R^2)-Z-Qn-Pm-CH(Ph)-NH_2$$

When $R^1$ is not methyl, the polymers can be treated to selectively remove either the $R^1$ protecting group or the methyl group to provide polymers of the formula:

$$R^1R^2N-Z-Qn-Pm-CH(Ph)-NH_2$$

(remove —$CH_3$)

$$HN(R^2)-Z-Qn-Pm-CH(Ph)-N(Me)H$$

(remove $R^1$) or $$H_2N-Z-Qn-Pm-CH(Ph)-N(Me)H$$

(remove $R^1$ and $R^2$, either simultaneously or sequentially).

Complete deprotection or removal of the protecting groups provides polymers of the formula $$H_2N-Z-Qn-Pm-CH(Ph)-NH_2$$

Another exemplary polymer in this aspect of the invention can have the structure:

$$R^1R^2N-Z-Qn-Pm-CH(Ph)-N(TMS)H$$

wherein TMS is trimethylsilyl. Again the various groups on the amine functionalities can be removed to provide polymers such as $$R^1R^2N-Z-Qn-Pm-CH(Ph)-NH_2$$

(remove the TMS group);

$$HN(R^2)-Z-Qn-Pm-CH(Ph)-N(TMS)H$$

(remove $R^1$); and $$H_2N-Z-Qn-Pm-CH(Ph)-N(TMS)H$$

(remove both $R^1$ and $R^2$, either simultaneously or sequentially).

Also in this embodiment of the invention, it is noted that the living polymer can be reacted with an imine and rather than isolating the resultant imine functionalized polymer as described above, an intermediate polymer of the formula

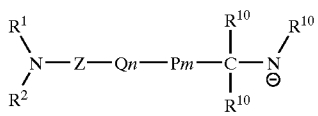

can be directed to an additional step in which the nitrogen atom is reacted with a suitable agent to form a polymer having to polymer segment or functionality as represented generally below:

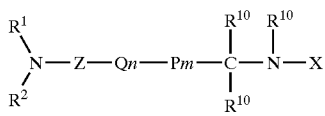

in which X is a polymer segment or functionality derived by reaction of a suitable reagent with the imine intermediate and $R^{10}$ attached to the N atom may be present or absent depending upon the reaction. For example, the intermediate polymer can be reacted with diisocyanate to form a polymer having at least one isocyanate group as illustrated below:

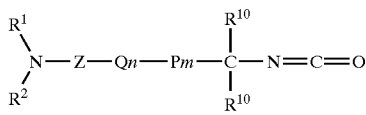

Particularly preferred polymers include polymers having telechelic primary and/or secondary amine groups, as well as their hydrogenated analogs. A primary amine results when all protecting groups are removed from a protected amine functionality. A secondary amine results when one but not another protecting group is removed from a protected amine functionality. The primary and secondary amine groups can be represented generally by the formula —N(H)R, in which R is hydrogen (primary amine) or $R^2$ as defined above (secondary amine).

The newly liberated primary or secondary amino groups can then participate in subsequent polymerization chemistry. For example, a mono primary or secondary amine and/or a telechelic primary or secondary diamine can react with a diisocyanate to afford a polyurethane. Advantageously the diisocyanate is a non-symmetrical diisocyanate, such as isophorone diisocyanate, as shown below:

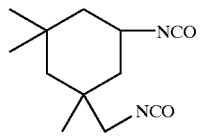

Preferably an excess amount of diisocyanate is used to minimize or prevent chain extension. After the diisocynate is reacted with the amine terminated polymer, the isocyanate groups on the terminal ends of the polymer may be blocked. This allows the polymers to be used in formulations with diols and other groups which normally react with isocyanates, such as coating systems either in solvents or aqueous systems. See U.S. Pat. No. 5,710,209.

The newly liberated primary or secondary amino groups can also react with an unreacted epoxy group (oxirane) groups to form partially or fully crosslinked epoxy resins. Similar to the diisocyanates, advantageously an unsymmetrical diepoxide reagent is used in excess amounts to minimize or prevent chain extension. An exemplary unsymmetrical diepoxide is

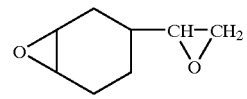

However, any diepoxide can be used, such as the diglycidyl ether of Bisphenol A (DGEBA). Other aromatic epoxies can be used such as the diglycidyl ether of Bisphenol F, or the diglycidyl ether of resorcinol. For improved thermal oxidative and UV stability, cycloaliphatic epoxies can be used.

In another aspect of the invention, one or more primary and/or secondary amines can be reacted with excess anhydride, such as maleic anhydride

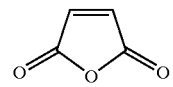

to form a polymer having one or more terminal carboxyl functionalities —COOH.

In yet another aspect of the invention, one or more primary or/and secondary amines can be reacted with glycidyl methacrylate

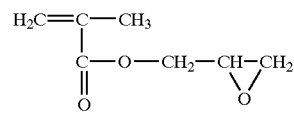

to form a polymer having one or more terminal olefinic groups —C(R)=CH$_2$, wherein R can be methyl).

In yet another aspect of the invention, one or more primary or/and secondary amines can be reacted with glycidol

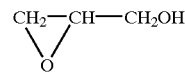

to provide a hydroxyl terminated polymer with an epoxy group.

Condensation polymers can also be prepared. For example, a polyamide condensation polymer can be synthesized from a telechelic diamine and a dicarboxylic acid.

The skilled artisan will appreciate that these and other reactions can be conducted on one or more terminal ends of the polymers of the invention.

In addition, when the living chain end is reacted with a protected functionalized electrophile, the resultant protected functionality can also be deprotected, and the liberated functionality can optionally be reacted with one or more comonomers to polymerize a functional end thereof. Exemplary comonomers include without limitation cyclic ethers, diamines, diisocyanates, polyisocyanates, di-, poly- and cyclic amides, di- and polycarboxylic acids, diols, polyols, anhydrides, and the like and mixtures thereof. For example, functionalized polymers can be further reacted with monofunctional monomers, such as caprolactam, or other lactams, to form a polyamide block polymer segment, or cyclic ethers such ethylene oxide to form polyether blocks; or with difunctional monomers, such as diacids or anhydrides and diamines to form polyamide blocks, or diacids or anhydrides or lactones and diols to form polyester blocks, or diols and polyols with diisocyanates or polyisocyanates to form polyurethane blocks. Polyisocyanates or polyfunctional polyols are examples of polyfunctional monomers. The functional group may also be reacted with a suitable agent containing a reactive olefinic bond, such as a styrenic or acrylic functionality, such as methacroyl chloride, which will act to change the nature of the functionality and provide a "macromonomer" capable of polymerizing with other free radically polymerizable monomers.

In yet another aspect of the invention, two or more living polymers can be linked using a coupling or linking agent as known in the art. In one embodiment of this aspect of the invention, the linking agent is a difunctional linking agent. The resultant homotelechelic polymer is represented by the below formula:

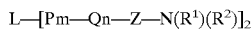

wherein:

each $R^1$, $R^2$, P, Q, Z, m and n independently have the meanings ascribed above; and L is a residue of a difunctional linking agent, such as $SiMe_2$ residue derived form the difunctional linking agent $SiMe_2Cl_2$.

In another embodiment of this aspect of the invention, the linking agent is a multifunctional linking agent. The resultant star or multi-branched polymer is represented by the below formula:

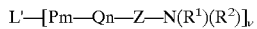

wherein:

each $R^1$, $R^2$, P, Q, Z, m and n independently have the meanings ascribed above;

L' is a residue of a multifunctional linking agent, such as divinylbenzene; and v is from 3 to 30. As the skilled artisan will appreciate, each $R^1$, $R^2$, P, Q, Z, m and n can differ if the coupled living polymers are prepared using different protected functionalized and/or non-functional initiators. Such polymers prepared using different protected functionalized initiators and/or non-functional initiators can be presented as follows:

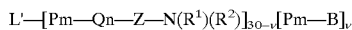

wherein:

$R^1$, $R^2$, P, Q, Z, m, n, L', and v have the meanings ascribed above; and each [Pm—B] can be the same or different and each P and m is as defined above and each B is independently selected from the residue of an alkyllithium initiator (i.e., a non-functional initiator) or a protected functionalized initiator, in which the protecting group is intact or removed. The skilled artisan will appreciate that each arm can be the same length or different lengths and can include the same or different monomer composition.

As discussed above, these homotelechelic and star or multi-branched polymers can be hydrogenated, deprotected and/or further reacted with one or more comonomers to form polymer segments. Particularly preferred polymers include homotelechelic and star or multibranched polymers having primary and/or secondary amine groups, as well as their hydrogenated analogs. As noted above, primary amines result from the removal of both protecting groups $R^1$ and $R^2$ and secondary amines result from the removal of protecting group $R^1$. The primary and secondary amine groups are represented generally by the formula —N(H)R, in which R is hydrogen (primary amine) or $R^2$ as defined above.

The molecular architecture of compounds of the present invention can be precisely controlled. The degree of functionality can be adjusted by simply varying the ratio of tertiary amino functional initiator to coupling agent. Further, the monomer identity, the monomer composition and molecular weight can be independently manipulated by varying the monomer charged. Finally, the number of polymer arms can be adjusted by varying the nature of the coupling agent, and the ratio of living polymer to the coupling agent.

Non-hydrogenated linear or radial polymers prepared with the amine initiators of the present invention, including homopolymers of dienes, block or random copolymers of different dienes, or block or random copolymers of dienes and alkenylsubstituted aromatic monomers, possessing tertiary amine functional groups, are useful for production of elastomeric compounds exhibiting reduced hysteresis characteristics. Introduction of functional groups, particularly amino functional groups to the termini of polymer chains of polymers used in tire compounds in particular, has resulted in lowered hysteresis properties which are associated with reduced rolling resistance and heat build-up during operation of the tire. Examples of the use of amine functional polymers for such applications are described in U.S. Pat. Nos. 5,959,048, 5,935,893, 5,932,662, 5,916,961, 5,912,343, 5,902,856, 5,880,206, 5,502,131, 5,496,940, 5,491,230, 5,332,810, 5,274,106, 5,238,893, 5,219,942, 5,216,080, 5,115,006, 4,614,771, the disclosures of which are incorporated herein by reference.

The present invention will be further illustrated by the following non-limiting examples.

Preparation of Initiators

EXAMPLE 1

Preparation of Initiator Precursor 3-[(N-benzyl-N-methyl)amino]-1-propylchloride To a stirred suspension of $K_2CO_3$ (200 g, 1.5 mole) in cyclohexane 200 mL and 1-bromo-3-chloropropane ("BCP") (540 g, 3.4 mole) was added dropwise over a period of 1 hour at 20° C. benzylmethyl amine (272 g, 2.24 mole). After complete addition the reaction was allowed to stir for an additional 20 hours. The crude reaction mixture was filtered and then washed with saturated NaCl (3×100 mL). The organic phase was extracted with 3N HCl (3×100 mL). The resulting aqueous phase, containing the desired product as the hydrochloric salt, was washed with hexanes (3×100 mL) to remove any residual BCP. The aqueous phase was subsequently basified with 50 wt % NaOH and extracted with cyclohexane (3×100 mL). After solvent removal 220 g (50% yield) of the title compound was isolated as a yellow oil.

EXAMPLE 2

Preparation of 3-[(N-benzyl-N-methyl)amino]-1-propyllithium

To a 500 ml Morton/cleave flask reactor under argon atmosphere was added lithium powder (13.32 g, 1.92 mole) and 141 grams of cyclohexane. To a constant addition funnel was added 3-[(N-benzyl-N-methyl)amino]-1-propylchloride (70.93 g, 0.34 mol) and 83.3 grams cyclohexane. Immediately before beginning the addition, the lithium metal mixture was heated to 53° C. using a heating mantel. Dropwise addition of the feed solution was performed while maintaining the reaction temperature at 50° C. A cooling bath of hexane, to which dry ice was added periodically, was employed to maintain a reaction temperature between 48° to 51° C. The total addition time was 1.22 hours with an average stirring rpm of 925. The reaction mixture was stirred at least one hour after the feed was completed. This mixture was then pumped through a ⅜" teflon tube to a pressure filter that contained about 10 grams of filter aid and filtered under an argon atmosphere. The reactor was then rinsed 3×50 ml cyclohexane, each time transferred to the muds that were also washed with the rinse. The final product was 420 g of light amber solution. Analysis by WE titration indicated a 99% yield of active base (0.809 mole/kg). GC-MS (TMS derivative): Calculated fragment masses: 235, 220, 134, 91, 73; Observed fragment masses: 235, 220, 134, 91, 73.

EXAMPLE 3

Preparation of Initiator Precursor 3-[(N,N-dibenzylamino]-1-propylchloride

To a stirred suspension of $K_2CO_3$ (200 g, 1.5 mole) in cyclohexane 200 mL and 1-bromo-3-chloropropane (540 gms, 3.4 mole) is added dropwise over a period of 1 h at 20° C. dibenzyl amine (442 g, 2.24 mole). After complete addition the reaction is allowed to stir for an additional 20 h. The crude reaction mixture is filtered and then washed with saturated NaCl (3×100 mL). The organic phase is extracted with 3N HCl (3×100 mL). The resulting aqueous phase, containing the desired product as the hydrochloric salt, is washed with hexanes (3×100 mL) to remove any residual BCP. The aqueous phase is subsequently basified with 50 wt % NaOH and extracted with cyclohexane (3×100 mL). After solvent removal 324 g (53% yield) of the title compound was isolated as a yellow oil.

EXAMPLE 4

Preparation of 3-[(N,N-dibenzylamino]-1-propyllithium

To a 500 ml Morton/cleave flask reactor under argon atmosphere is added lithium powder (13.32 g, 1.92 mole) and 141 grams of cyclohexane. To a constant addition funnel is added 3-[(N,N-dibenzylamino]-1-propylchloride (92.8 g, 0.34 mol) and 83.3 grams cyclohexane. Immediately before beginning the addition, the lithium metal mixture is heated to 53° C. using a heating mantel. Dropwise addition of the feed solution is performed while maintaining the reaction temperature at 50° C. A cooling bath of hexane, to which dry ice is added periodically, is employed to maintain a reaction temperature between 48° to 51° C. The total addition time is 1.22 hours with an average stirring rpm of 925. The reaction mixture is stirred at least one hour after the feed was completed. This mixture is then pumped through a ⅜" teflon tube to a pressure filter that contains about 10 grams of filter aid and is filtered under an argon atmosphere. The reactor is then rinsed 3×50 ml cyclohexane, each time transferred to the muds that were also washed with the rinse. The final product is 420 g of light amber solution. Analysis by WE titration indicates a 99% yield of active base (0.809 mole/kg).

EXAMPLE 5

Preparation of Initiator Precursor 3-[(N-t-Butyl-N-methyl)amino]-1-propylchloride To a stirred suspension of $K_2CO_3$ (200 g, 1.5 mole) in cyclohexane 200 mL and 1-bromo-3-chloropropane (540 gms, 3.4 mole) is added dropwise over a period of 1 h at 20° C. t-butylmethyl amine (194 g, 2.24 mole). After complete addition the reaction is allowed to stir for an additional 20 h. The crude reaction mixture is filtered and then washed with saturated NaCl (3×100 mL). The organic phase is extracted with 3N HCl (3×100 mL). The resulting aqueous phase, containing the desired product as the hydrochloric salt, is washed with hexanes (3×100 mL) to remove any residual BCP. The aqueous phase is subsequently basified with 50 wt % NaOH and extracted with cyclohexane (3×100 mL). After solvent removal 186 g (51% yield) of the title compound is isolated as a yellow oil.

EXAMPLE 6

Preparation of 3-[(N-t-Butyl-N-methyl)amino]-1-propyllithium

To a 500 ml Morton/cleave flask reactor under argon atmosphere is added lithium powder (13.32 g, 1.92 mole) and 141 grams of cyclohexane. To a constant addition funnel was added 3-[(N-t-Butyl-N-methyl)amino]-1-propylchoride (55.6 g, 0.34 mol) and 83.3 grams cyclohexane. Immediately before beginning the addition, the lithium metal mixture is heated to 53° C. using a heating mantel. Dropwise addition of the feed solution is performed while maintaining the reaction temperature at 50° C. A cooling bath of hexane, to which dry ice is added periodically, is employed to maintain a reaction temperature between 48° to 51° C. The total addition time is 1.22 hours with an average stirring rpm of 925. The reaction mixture is stirred at least one hour after the feed is completed. This mixture is then pumped through a ⅜" teflon tube to a pressure filter that contains about 10 grams of filter aid and filtered under an argon atmosphere. The reactor is then rinsed 3×50 ml cyclohexane, each time transferred to the muds that are also washed with the rinse. The final product is 420 g of light amber solution. Analysis by WE titration indicated a 99% yield of active base (0.809 mole/kg).

EXAMPLE 7

Preparation of Initiator Precursor 3-[(N,N-di-t-Butyl)amino]-1-propylchloride

To a stirred suspension of $K_2CO_3$ (200 g, 1.5 mole) in cyclohexane 200 mL and 1-bromo-3-chloropropane (540 gms, 3.4 mole) is added dropwise over a period of 1 h at 20° C. di-t-butyl amine (289 g, 2.24 mole). After complete addition the reaction is allowed to stir for an additional 20 h. The crude reaction mixture is filtered and then washed with saturated NaCl (3×100 mL). The organic phase is extracted with 3N HCl (3×100 mL). The resulting aqueous phase, containing the desired product as the hydrochloric salt, is washed with hexanes (3×100 mL) to remove any residual BCP. The aqueous phase is subsequently basified with 50 wt % NaOH and extracted with cyclohexane (3×100 mL). After solvent removal 234 g (51% yield) of the title compound is isolated as a yellow oil.

EXAMPLE 8

Preparation of 3-[(N,N-di-t-Butyl)amino]-1-propyllithium

To a 500 ml Morton/cleave flask reactor under argon atmosphere is added lithium powder (13.32 g, 1.92 mole) and 141 grams of cyclohexane. To a constant addition funnel is added 3-[(N,N-di-t-butyl)amino]-1-propylchoride (69.7 g, 0.34 mol) and 83.3 grams cyclohexane. Immediately before beginning the addition, the lithium metal mixture is heated to 53° C. using a heating mantel. Dropwise addition of the feed solution is performed while maintaining the reaction temperature at 50° C. A cooling bath of hexane, to which dry ice is added periodically, is employed to maintain a reaction temperature between 48° to 51° C. The total addition time is 1.22 hours with an average stirring rpm of 925. The reaction mixture is stirred at least one hour after the feed is completed. This mixture is then pumped through a ⅜" teflon tube to a pressure filter that contains about 10 grams of filter aid and filtered under an argon atmosphere. The reactor is then rinsed 3×50 ml cyclohexane, each time transferred to the muds that were also washed with the rinse. The final product is 428.90 g of light amber solution. Analysis by WE titration indicated a 99% yield of active base (0.809 mole/kg).

Preparation of Polymers

EXAMPLE 9

Preparation of Protected-Alpha-3° Amine Functionalized Polyisoprene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N-benzyl-N-methyl)amino]-1-propyllithium 0.82 mmoles (0.14 grams active of 14.0 wt % in cyclohexane), and purified cyclohexane (195 g). The reactor is then flame sealed off. Diethylether 23 grams (0.31 mole) was added from a break-seal ampoule. Purified isoprene monomer (10.20 grams, 150 mmoles) is added from a break-seal ampoule. The reaction mixture is stirred for twenty four hours at room temperature. The living, functionalized poly(isoprenyl)lithium is terminated with degassed methanol from the last ampoule. 2,6-Di-tert-butyl-4-methylphenol (BHT, 0.01%) is added to the polymer solution as an antioxidant. The resultant protected, functionalized polymer is isolated by concentration of the organic solution. The resultant functionalized polyisoprene polymer is characterized by SEC (polyisoprene standards), and had the following properties: $M_n$=5,200 g/mole, $M_w$=5,300 g/mole, $M_w/M_n$=1.03. $^1$H NMR verifies a microstructure of 55% 1,4 enchainment, and the presence of the benzyl protecting group on the amine functionality.

EXAMPLE 10

Preparation of Alpha-2° Amine Functionalized Polyisoprene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N-benzyl-N-methyl)amino]-1-propyllithium 0.82 mmoles (0.14 grams active of 14.0 wt % in cyclohexane), and purified cyclohexane (195 g). The reactor is then flame sealed off. Diethylether 23 grams (0.31 mole) was added from a break-seal ampoule. Purified isoprene monomer (10.20 grams, 150 mmoles) is added from a break-seal ampoule. The reaction mixture is stirred for twenty four hours at room temperature. The resulting reaction mixture is transferred to a 500 mL autoclave and sparged with hydrogen at 45° C. The reactor is pressurized to 700 psig with hydrogen and a Ni/Al catalyst is added slowly to control the resulting exothermic reaction. Enough catalyst is added to achieve a solution concentration of nickel to 100 ppm. (The catalyst is prepared in advance by reacting 1 molar eq. of nickel(II) 2-ethylhexanote with 2 molar eq. of triethylaluminum in cyclohexane). After 2 hr of hydrogenation, the reaction is allowed to cool to room temperature, depressurized and purged with nitrogen. The resultant functionalized polymer is precipitated into a large amount of methanol, filtered and washed with additional methanol. The resultant hydrogenated functionalized polyisoprene polymer is characterized by $^1$H NMR which verifies near quantitative hydrogenation (>97%) of the unsaturation in the backbone and deprotection (>97%) of the benzyl protecting group from the amine functionality to afford an alpha secondary amine.

EXAMPLE 11

Preparation of Alpha, Omega-2° Amine Functionalized Polyisoprene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N-benzyl-N-methyl)amino]-1-propyllithium 0.82 mmoles (0.14 grams active of 14.0 wt % in cyclohexane), and purified cyclohexane (195 g). The reactor is then flame sealed off. Diethylether 23 grams (0.31 mole) is added from a break-seal ampoule. Purified isoprene monomer (10.20 grams, 150 mmoles) is added from a break-seal ampoule. The reaction mixture is stirred for twenty four hours at room temperature. To the living polymer is added 3-[(N-benzyl-N-methyl)amino]-1-propylchoride (0.16 g, 0.9 mmoles) and is stirred for an additional 15 h at room temperature. The resulting reaction mixture is transferred to a 500 mL autoclave and sparged with hydrogen at 45° C. The reactor is pressurized to 700 psig with hydrogen and a Ni/Al catalyst is added slowly to control the resulting exothermic reaction. Enough catalyst is added to achieve a solution concentration of nickel to 100 ppm. (The catalyst is prepared in advance by reacting 1 molar eq. of nickel(II) 2-ethylhexanote with 2 molar eq. of triethylaluminum in cyclohexane). After 2 hr of hydrogenation, the reaction is allowed to cool to room temperature, depressurized and purged with nitrogen. The resultant hydrogenated functionalized polyisoprene polymer is characterized by $^1$H NMR which verifies near quantitative hydrogenation (>97%) of the unsaturation in the backbone and deprotection (>97%) of the benzyl protecting groups from the amine functionality to afford saturated polyisoprene with alpha, omega secondary amine functionalities.

EXAMPLE 12

Preparation of Protected-Alpha-3° Amine Functionalized-Polybutadiene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N-benzyl-N-methyl)amino]-1-propyllithium 0.82 mmoles (0.14 grams active of 14.0 wt % in cyclohexane), and purified cyclohexane (195 g). The reactor is then flame sealed off. Diethylether 23 grams (0.31 mole) was added from a break-seal ampoule. Purified butadiene monomer (8.10 grams, 150 mmoles) is added from a break-seal ampoule. The reaction mixture is stirred for twenty four hours at room temperature. The living, functionalized poly(butadienyl)lithium is terminated with degassed methanol from the last ampoule. 2,6-Di-tert-butyl-4-methylphenol (BHT, 0.01%) is added to the polymer solution as an antioxidant. The resultant protected, functionalized polymer is isolated by concentration of the organic solution. The resultant functionalized polybutadiene polymer is characterized by SEC (polybutadiene standards), and had the following properties: $M_n$=5,200 g/mole, $M_w$=5,300 g/mole, $M_w/M_n$=1.03. $^1$H NMR indicates the microstructure is 55% 1,4 enchainment, and the presence of the benzyl protecting group on the amine functionality.

EXAMPLE 13

Preparation of Alpha-2° Amine Functionalized Polybutadiene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N-benzyl-N-methyl)amino]-1-propyllithium 0.82 mmoles (0.14 grams active of 14.0 wt % in cyclohexane), and purified cyclohexane (195 g). The reactor is then flame sealed off. Diethylether 23 grams (0.31 mole) was added from a break-seal ampoule. Purified butadiene monomer (8.10 grams, 150 mmoles) is added from a break-seal ampoule. The reaction mixture is stirred for twenty four hours at room temperature. The resulting reaction mixture is transferred to a 500 mL autoclave and sparged with hydrogen at 45° C. The reactor is pressurized to 700 psig with hydrogen and a Ni/Al catalyst is added slowly to control the resulting exothermic reaction. Enough catalyst is added to achieve a solution concentration of nickel to 100 ppm. The catalyst is prepared in advance by reacting 1 molar eq. of nickel(II) 2-ethylhexanote with 2 molar eq. of triethylaluminum in cyclohexane). After 2 hr of hydrogenation, the reaction is allowed to cool to room temperature, depressurized and purged with nitrogen. The resultant functionalized polymer is precipitated into a large amount of methanol, filtered and washed with additional methanol. The resultant hydrogenated functionalized polybutadiene polymer is characterized by $^1$H NMR indicating near quantitative hydrogenation (>97%) of the unsaturation in the backbone and deprotection (>97%) of the benzyl protecting group from the amine functionality to afford a terminal secondary amine.

EXAMPLE 14

Preparation of Alpha, Omega-2° Amine Functionalized Polybutadiene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N-benzyl-N-methyl)amino]-1-propyllithium 0.82 mmoles (0.14 grams active of 14.0 wt % in cyclohexane), and purified cyclohexane (195 g). The reactor is then flame sealed off. Diethylether 23 grams (0.31 mole) is added from a break-seal ampoule. Purified butadiene monomer (8.10 grams, 150 mmoles) is added from a break-seal ampoule. The reaction mixture is stirred for twenty four hours at room temperature. To the living polymer is added 3-[(N-benzyl-N-methyl)amino]-1-propylchloride (0.16 g, 0.9 mmoles) and is stirred for an additional 15 h at room temperature. The resulting reaction mixture is transferred to a 500 mL autoclave and sparged with hydrogen at 45° C. The reactor is pressurized to 700 psig with hydrogen-and a Ni/Al catalyst is added slowly to control the resulting exothermic reaction. Enough catalyst is added to achieve a solution concentration of nickel to 100 ppm. (The catalyst is prepared in advance by reacting 1 molar eq. of nickel(II) 2-ethylhexanote with 2 molar eq. of triethylaluminum in cyclohexane). After 2 hr of hydrogenation, the reaction is allowed to cool to room temperature, depressurized and purged with nitrogen. The resultant hydrogenated functionalized polybutadiene polymer is characterized by $^1$H NMR which verifies near quantitative hydrogenation (>97%) of the unsaturation in the backbone and deprotection (>97%) of the benzyl protecting groups from the amine functionality to afford saturated polybutadiene with alpha, omega secondary amine functionalities.

EXAMPLE 15

Preparation of Protected-Alpha-3° Amine Functionalized Polyisoprene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N,N-dibenzylamino]-1-propyllithium 0.82 mmoles (0.16 grams active of 14.0 wt % in cyclohexane), and purified cyclohexane (195 g). The reactor is then flame sealed off. Diethylether 23 grams (0.31 mole) is added from a break-seal ampoule. Purified isoprene monomer (10.20 grams, 150 mmoles) is added from a break-seal ampoule. The reaction mixture is stirred for twenty four hours at room temperature. The living, functionalized poly(isoprenyl)lithium is terminated with degassed methanol from the last ampoule. 2,6-Di-tert-butyl-4-methylphenol (BHT, 0.01%) is added to the polymer solution as an antioxidant. The resultant protected, functionalized polymer is isolated by concentration of the organic solution. The resultant functionalized polyisoprene polymer is characterized by SEC (polyisoprene standards), and had the following properties: $M_n$=5,200 g/mole, $M_w$=5,300 g/mole, $M_w/M_n$=1.03. $^1$H NMR verifies a microstructure of 55% 1,4 enchainment, and the presence of the benzyl protecting group on the amine functionality.

EXAMPLE 16

Preparation of Alpha-1° Amine Functionalized Polyisoprene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N,N-dibenzylamino]-1-propyllithium 0.82 mmoles (0.16 grams active of 14.0 wt % in cyclohexane), and purified cyclohexane (195 g). The reactor is then flame sealed off. Diethylether 23 grams (0.31 mole) was added from a break-seal ampoule. Purified isoprene monomer (10.20 grams, 150 mmoles) is added from a break-seal ampoule. The reaction mixture is stirred for twenty four hours at room temperature. The resulting reaction mixture is transferred to a 500 mL autoclave and sparged with hydrogen at 45° C. The reactor is pressurized to 700 psig with hydrogen and a Ni/Al catalyst is added slowly to control the resulting exothermic reaction. Enough catalyst is added to achieve a solution concentration of nickel to 100 ppm. (The catalyst is prepared in advance by reacting 1 molar eq. of nickel(II) 2-ethylhexanote with 2 molar eq. of triethylaluminum in cyclohexane). After 2 hr of hydrogenation, the reaction is allowed to cool to room temperature, depressurized and purged with nitrogen. The resultant functionalized polymer is precipitated into a large amount of methanol, filtered and washed with additional methanol. The resultant hydrogenated functionalized polyisoprene polymer is characterized by $^1$H NMR which verifies near quantitative hydrogenation (>97%) of the unsaturation in the backbone and deprotection (>97%) of the benzyl protecting group from the amine functionality to afford a terminal primary amine.

EXAMPLE 17

Preparation of Alpha, Omega-1° Amine Functionalized Polyisoprene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N,N-dibenzylamino]-1-propyllithium 0.82 mmoles (0.16 grams active of 14.0 wt % in cyclohexane), and purified cyclohexane (195 g). The reactor is then flame sealed off. Diethylether 23 grams (0.31 mole) was added from a break-seal ampoule. Purified isoprene monomer (10.20 grams, 150 mmoles) is added from a break-seal ampoule. The reaction mixture is stirred for twenty four hours at room temperature. To the living polymer is added 3-[(N,N-dibenzylamino]-1-propylchloride (0.25 g, 0.9 mmoles) and is stirred for an additional 15 h at room temperature. The resulting reaction mixture is transferred to a 500 mL autoclave and sparged with hydrogen at 45° C. The reactor is pressurized to 700 psig with hydrogen and a Ni/Al catalyst is added slowly to control the resulting exothermic reaction. Enough catalyst is added to achieve a solution concentration of nickel to 100 ppm. (The catalyst is prepared in advance by reacting 1 molar eq. of nickel(II) 2-ethylhexanote with 2 molar eq. of triethylaluminum in cyclohexane). After 2 hr of hydrogenation, the reaction is allowed to cool to room temperature, depressurized and purged with nitrogen. The resultant hydrogenated functionalized polyisoprene polymer is characterized by $^1$H NMR which verifies near quantitative hydrogenation (>97%) of the unsaturation in the backbone and deprotection (>97%) of the benzyl protecting groups from the amine functionality to afford saturated polyisoprene with alpha, omega primary amine functionalities.

EXAMPLE 18

Preparation of Protected-Alpha-3° Amine Functionalized-Polybutadiene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N,N-dibenzylamino]-1-propyllithium 0.82 mmoles (0.16 grams active of 14.0 wt % in cyclohexane), and purified cyclohexane (195 g). The reactor is then flame sealed off. Diethylether 23 grams (0.31 mole) was added from a break-seal ampoule. Purified butadiene monomer (8.10 grams, 150 mmoles) is added from a break-seal ampoule. The reaction mixture is stirred for twenty four hours at room temperature. The living, functionalized poly(butadienyl)lithium is terminated with degassed methanol from the last ampoule. 2,6-Di-tert-butyl-4-methylphenol (BHT, 0.01%) is added to the polymer solution as an antioxidant. The resultant protected, functionalized polymer is isolated by concentration of the organic solution. The resultant functionalized polybutadiene polymer is characterized by SEC (polybutadiene standards), and had the following properties: $M_n$=5,200 g/mole, $M_w$=5,300 g/mole, $M_w/M_n$=1.03. $^1$H NMR indicates the microstructure is 55% 1,4 enchainment, and the presence of the benzyl protecting groups on the amine functionality.

EXAMPLE 19

Preparation of Alpha-1° Amine Functionalized Polybutadiene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N,N-dibenzylamino]-1-propyllithium 0.82 mmoles (0.16 grams active of 14.0 wt % in cyclohexane), and purified cyclohexane (195 g). The reactor is then flame sealed off. Diethylether 23 grams (0.31 mole) was added from a break-seal ampoule. Purified butadiene monomer (8.10 grams, 150 mmoles) is added from a break-seal ampoule. The reaction mixture is stirred for twenty four hours at room temperature. The resulting reaction mixture is transferred to a 500 mL autoclave and sparged with hydrogen at 45° C. The reactor is pressurized to 700 psig with hydrogen and a Ni/Al catalyst is added slowly to control the resulting exothermic reaction. Enough catalyst is added to achieve a solution concentration of nickel to 100 ppm. (The catalyst is prepared in advance by reacting 1 molar eq. of nickel (II) 2-ethylhexanote with 2 molar eq. of triethylaluminum in cyclohexane). After 2 hr of hydrogenation, the reaction is allowed to cool to room temperature, depressurized and purged with nitrogen. The resultant functionalized polymer is precipitated into a large amount of methanol, flittered and washed with additional methanol. The resultant hydrogenated functionalized polybutadiene polymer is characterized by $^1$H NMR verifying near quantitative hydrogenation (>97%) of the unsaturation in the backbone and deprotection (>97%) of the benzyl protecting groups from the amine functionality to afford an alpha primary amines.

EXAMPLE 20

Preparation of Alpha, Omega-2° Amine Functionalized Polybutadiene

A 500 ml. glass reactor is equipped with three break-seal reagent ampoules, a sampling port attached with a Teflon® stopcock, an inlet tube fitted with a septum cap, and a magnetic stir bar. This reactor is flame sealed to a high vacuum line, and evacuated at 120° C. for 8 hours. The flask is refilled with dry argon, and allowed to cool to room temperature. The reactor is charged with 3-[(N,N-dibenzylamino]-1-propyllithium 0.82 mmoles (0.16 grams active of 14.0 wt % in cyclohexane), and purified cyclohexane (195 g). The reactor is then flame sealed off. Diethylether 23 grams (0.31 mole) was added from a break-seal ampoule. Purified butadiene monomer (8.10 grams, 150 mmoles) is added from a break-seal ampoule. The reaction mixture is stirred for twenty four hours at room temperature. To the living polymer is added 3-[(N,N-dibenzylamino]-1-propylchloride (0.25 g, 0.9 mmoles) and is stirred for an additional 15 h at room temperature. The resulting reaction mixture is transferred to a 500 mL autoclave and sparged with hydrogen at 45° C. The reactor is pressurized to 700 psig with hydrogen and a Ni/Al catalyst is added slowly to control the resulting exothermic reaction. Enough catalyst is added to achieve a solution concentration of nickel to 100 ppm. (The catalyst is prepared in advance by reacting 1 molar eq. of nickel (II) 2-ethylhexanote with 2 molar eq. of triethylaluminum in cyclohexane). After 2 hr of hydrogenation, the reaction is allowed to cool to room temperature, depressurized and purged with nitrogen. The resultant hydrogenated functionalized polybutadiene polymer is characterized by $^1$H NMR which indicates near quantitative hydrogenation (>97%) of the unsaturation in the backbone and deprotection (>97%) of the benzyl protecting groups from the amine functionality to afford saturated polybutadiene with alpha, omega primary amine functionalities.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A compound of the formula:

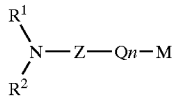

wherein:
M is an alkali metal selected from the group consisting of lithium, sodium and potassium;
Z is a branched or straight chain hydrocarbon connecting group which contains 3–25 carbon atoms, optionally substituted with aryl or substituted aryl;
Q is a saturated or unsaturated hydrocarbyl group derived by the incorporation of one or more unsaturated organic compounds into the M—Z linkage;
n is from 0 to 5;
$R^1$ is selected from the group consisting of aralkyl, allyl, and tertiary alkyl; and
$R^2$ is the same as $R^1$, or when $R^1$ is benzyl $R^2$ is different from $R^1$ and selected from the group consisting of alkyl, substituted alkyl, alkoxy, substituted alkoxy, aryl, substituted aryl, heteroaryl, substituted heteroaryl, cycloalkyl, substituted cycloalkyl, heterocycloalkyl, and substituted heterocycloalkyl, with the proviso that when $R^2$ is not the same as $R^1$, then $R^2$ is more stable under conditions used to remove $R^1$,
or $R^1$ and $R^2$ together with the nitrogen atom to which they are attached form

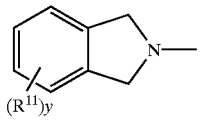

wherein y is from 1 to 4 and each $R^{11}$ is independently selected from the group consisting of hydrogen, alkyl, substituted alkyl, aryl, substituted aryl, cycloalkyl, substituted cycloalkyl, alkoxy, substituted alkoxy, heteroaryl, substituted heteroaryl, heterocycloalkyl, and substituted heterocycloalkyl.

2. The compound of claim 1, wherein $R^1$ is benzyl or benzyl derivative.

3. The compound of claim 1, wherein $R^1$ is tertiary alkyl.

4. The compound of claim 3 wherein $R^1$ is tertiary butyl.

5. The compound of claim 1, wherein $R^2$ is the same as $R^1$.

6. The compound of claim 1, wherein $R^2$ is methyl.

7. The compound of claim 1, wherein $R^1$ and $R^2$ together with the nitrogen atom to which they are attached form

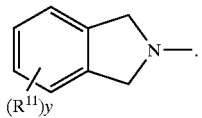

8. The compound of claim 7, wherein each $R^{11}$ is hydrogen.

9. The compound of claim 1, wherein M is lithium.

10. The compound of claim 1, wherein M is sodium.

11. The compound of claim 1, wherein M is potassium.

12. The compound of claim 1, wherein n is greater than 0 and wherein Q is derived by incorporation of one or more compounds selected from the group consisting of conjugated diene hydrocarbons, alkenylsubstituted aromatic compounds, and mixtures thereof.

13. The compound of claim 12, wherein said conjugated diene is selected from the group consisting of 1,3-butadiene, isoprene, 2,3-dimethyl-1,3-butadiene, 1,3-pentadiene (piperylene), myrcene, 2-methyl-3-ethyl-1,3-butadiene, 2-methyl-3-ethyl-1,3-pentadiene, 1,3-hexadiene, 2-methyl-1,3-hexadiene, 1,3-heptadiene, 3-methyl-1,3-heptadiene, 1,3-octadiene, 3-butyl-1,3-octadiene, 3,4-dimethyl-1,3-hexadiene, 3-n-propyl-1,3-pentadiene, 4,5-diethyl-1,3-octadiene, 2,4-diethyl-1,3-butadiene, 2,3-di-n-propyl-1,3-butadiene, 2-methyl-3-isopropyl-1,3-butadiene, and mixtures thereof.

14. The compound of claim 12, wherein said alkenylsubstituted aromatic compound is selected from the group consisting of styrene, alpha-methylstyrene, vinyltoluene, 2-vinylpyridine, 4-vinylpyridine, 1-vinylnaphthalene, 2-vinylnaphthalene, 1-alpha-methylvinylnaphthalene, 2-alpha-methylvinylnaphathalene, 1,2-diphenyl-4-methyl-1-hexene, alkyl, cycloalkyl, aryl, alkaryl and aralkyl derivatives thereof and mixtures thereof.

* * * * *